(12) United States Patent
Watanabe et al.

(10) Patent No.: US 11,746,078 B2
(45) Date of Patent: Sep. 5, 2023

(54) KINETIC RESOLUTION REACTION OF A (1RS,2SR)-(2-HYDROXY-3,5,5-TRIMETHYL-3-CYCLOPENTENYL)METHYL CARBOXYLATE COMPOUND, A PROCESS FOR PREPARING OPTICALLY ACTIVE TRANS-α-NECRODYL ISOBUTYRATE, AND A PROCESS FOR PREPARING OPTICALLY ACTIVE γ-NECRODYL ISOBUTYRATE

(71) Applicant: Shin-Etsu Chemical Co., Ltd., Tokyo (JP)

(72) Inventors: Tomohiro Watanabe, Joetsu (JP); Takeshi Kinsho, Joetsu (JP); Takeru Watanabe, Joetsu (JP); Miyoshi Yamashita, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/580,874

(22) Filed: Jan. 21, 2022

(65) Prior Publication Data
US 2022/0234983 A1     Jul. 28, 2022

(30) Foreign Application Priority Data

Jan. 26, 2021   (JP) ................. 2021-010360

(51) Int. Cl.
*C07C 67/08*   (2006.01)

(52) U.S. Cl.
CPC .......... *C07C 67/08* (2013.01); *C07C 2601/10* (2017.05)

(58) Field of Classification Search
CPC . C07C 2601/10; C07C 67/08; C07C 29/1285; C07C 33/12; C07C 36/06; C07C 67/14; C07C 67/293; C07C 67/297; C07C 67/60; C07C 69/24; C07C 69/28; C07B 2200/07
See application file for complete search history.

(56) References Cited

PUBLICATIONS

Zhou et al. ("Synthesis and Bioassay of Racemic and Chiral trans-a-Necrodyl Isobutyrate, the Sex Pheromone of the Grape Mealybug *Pseudococcus maritimus*", J. Agric. Food Chem., 58(8), 4977-4982, Published 2010). (Year: 2010).*
Extended European Search Report corresponding to European Patent Application No. 22152518.1 (5 pages) (dated Jun. 28, 2022).
Brecher, Jonathan "Graphical representation of stereochemical configuration (IUPAC Recommendations 2006)", Pure and Applied Chemistry, 78(10), 2006, 1897-1970.
Franco, José Carlos et al. "Novel Approaches for the Management of Mealybug Pests", Ishaaya I., Horowitz A. (eds) Biorational Control of Arthropod Pests. Springer, Dordrecht, 2009, 233-278.
Levi-Zada, Anat et al. "Identification of the Sex Pheromone of the Spherical Mealybug *Nipaecoccus viridis*", Journal of Chemical Ecology, 45(5), 2019, 455-463.
Millar, Jocelyn G. et al. "Chapter 2: Chemistry and Applications of Mealybug Sex Pheromones", ACS Symposium Series., vol. 906, 2005, 11-27.

(Continued)

*Primary Examiner* — Yevgeny Valenrod
*Assistant Examiner* — Blaine G Doletski
(74) *Attorney, Agent, or Firm* — Myers Bigel, P.A.

(57) ABSTRACT

The present invention relates to a process for preparing a (1S,2R)-(2-hydroxy-3,5,5-trimethyl-3-cyclopentenyl) methyl carboxylate compound of the following general formula (S,R)-(2), wherein $R^1$ represents a monovalent hydrocarbon group having 1 to 6 carbon atoms, and a bold wedged bond represents the absolute configuration, and a (1R,2S)-(2-acetoxy-3,5,5-trimethyl-3-cyclopentenyl)methyl carboxylate compound of the following general formula (R,S)-(3), wherein $R^1$ is as defined above, a hashed wedged bond represents the absolute configuration, and Ac represents an acetyl group, the process comprising: subjecting a (1RS,2SR)-(2-hydroxy-3,5,5-trimethyl-3-cyclopentenyl) methyl carboxylate compound of the following general formula (RS,SR)-(2), wherein $R^1$ is as defined above, and a hashed unwedged bond represents a relative configuration, to a kinetic resolution reaction with a lipase in the presence of vinyl acetate to obtain the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)).

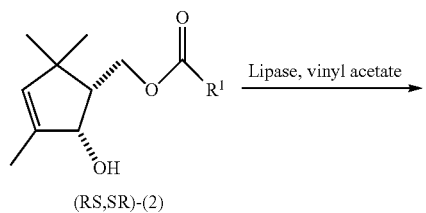

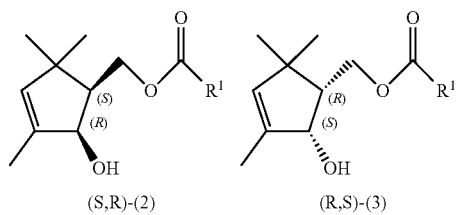

5 Claims, No Drawings

(56) References Cited

PUBLICATIONS

Ohtani, Ikuko et al. "High-field FT NMR application of Mosher's method. The absolute configurations of marine terpenoids", J. Am. Chem. Soc., 113(11), 1991, 4092-4096.
Ross, Laura et al. "Scale insects", Current Biology, 19(5), 2009, R184-R186.
Tabata, Jun et al. "Sex pheromone of a coccoid insect with sexual and asexual lineages: fate of an ancestrally essential sexual signal in parthenogenetic females", Journal of the Royal Society Interface, 14(128), 2017, 1-11.
Tabata, Jun et al. "Sexual attractiveness and reproductive performance in ageing females of a coccoid insect", Biology Letters, 14(7), 2018, 1-5.
Zhou, Yunfan et al. "Synthesis and Bioassay of Racemic and Chiral trans-α-Necrodyl Isobutyrate, the Sex Pheromone of the Grape Mealybug *Pseudococcus maritimus*", J. Agric. Food Chem., 58(8), 2010, 4977-4982.
Zou, Yunfan et al. "Chemistry of the pheromones of mealybug and scale insects", Nat. Prod. Rep., 32, 2015, 1067-1113.

\* cited by examiner

KINETIC RESOLUTION REACTION OF A (1RS,2SR)-(2-HYDROXY-3,5,5-TRIMETHYL-3-CYCLOPENTENYL)METHYL CARBOXYLATE COMPOUND, A PROCESS FOR PREPARING OPTICALLY ACTIVE TRANS-α-NECRODYL ISOBUTYRATE, AND A PROCESS FOR PREPARING OPTICALLY ACTIVE γ-NECRODYL ISOBUTYRATE

TECHNICAL FIELD

The present invention relates to a kinetic resolution reaction of a (1RS,2SR)-(2-hydroxy-3,5,5-trimethyl-3-cyclopentenyl)methyl carboxylate compound, a process for preparing optically active trans-α-necrodyl isobutyrate, and a process for preparing optically active γ-necrodyl isobutyrate.

BACKGROUND ART trans-α-Necrodyl isobutyrate, i.e., (1RS,4RS)-(3,4,5,5-tetramethyl-2-cyclopentenyl)methyl isobutyrate, and γ-necrodyl isobutyrate, i.e., (2,2,3,4-tetramethyl-3-cyclopentenyl)methyl isobutyrate, are known as pheromones, which are bioactive substances. For instance, (1R,4R)-α-necrodyl isobutyrate and (1S,4S)-α-necrodyl isobutyrate were identified as sex pheromones of grape mealybug (scientific name: *Pseudococcus maritimus*) (Non-Patent Literature 1 listed below). γ-Necrodyl isobutyrate was also identified as a sex pheromone of spherical mealybug (scientific name: *Nipaecoccus viridis*) (Non-Patent Literature 2 listed below).

Sex pheromones of insects are biologically active substances which usually have a function for females to attract males. Even a small amount of them exhibits a high attracting activity. Many applications for managing pests with the sex pheromones have been devised and practiced. For instance, the sex pheromones are widely used as a means for forecasting outbreak of pests, confirming geographic spread (invasion into a specific area), and for controlling pests. Widely used methods of controlling pests are a mass trapping method, a lure-and-kill or attract-and-kill method, a lure-and-infect or attract-and-infect method, and a mating disruption method. Trapping with a sex pheromone exhibits high attracting ability and is species-specific and, therefore, is very useful for detecting and monitoring pests of interest.

Mealybugs are small insects which suck plant juice. Some species of them seriously damage grains and fruit plants and are agriculturally serious insects. Mealybugs live, attaching to plant tissues such as knots or remains of flower parts, and therefore, are often difficult to find. Accordingly, it is difficult to find and remove mealybugs in plant quarantine for crops. Accordingly, sex pheromone-based traps are much useful for controlling mealybugs.

Adult female mealybugs do not have wings, and have degenerated legs and, accordingly, transfer only a little. Adult male mealybugs have wings, but are tiny and fragile, eat nothing after eclosion and, therefore, survive for a maximum of several days (Non-Patent Literatures 3 and 4 listed below). A sex pheromone released from such less-mobile females is essential to attract such short-lived males, and plays a key role in finding a mating partner. Therefore, its sex pheromone is believed to be under high selective pressure in evolution (Non-Patent Literatures 5 and 6 listed below). In fact, pheromones of mealybugs have highly species-specific structure and are very diverse (Non-Patent Literatures 7 and 8 listed below). Therefore, the sex pheromones of mealybugs are a useful means for pest control and pest quarantine and also are an important model for researching variation of chemical communication mechanisms of insects.

A process of Millar et al. is known for synthesizing optically active trans-α-necrodyl isobutyrate (Non-Patent Literature 1). A process for synthesizing one of the enantiomers of γ-necrodyl isobutyrate was reported by Levi-Zada et al. (Non-Patent Literature 2).

LIST OF THE LITERATURES

Non-Patent Literatures

[Non-Patent Literature 1] J. G. Millar et al., J. Agric. Food Chem., 2010, 58, 4977-4982.
[Non-Patent Literature 2] A. Levi-Zada et al., J. Chem. Ecol., 2019, 45, 455-463.
[Non-Patent Literature 3] J. C. Franco et al., Biorational Control of Arthropod Pests; I. Ishaaya, A. R. Horowitz, Eds., Springer, Dordrecht, 2009, 233-278.
[Non-Patent Literature 4] L. Ross et al., Curr. Biol., 2009, 19, R184-R186.
[Non-Patent Literature 5] J. Tabata et al., J. R. Soc. Interface, 2017, 14, 20170027.
[Non-Patent Literature 6] J. Tabata et al., Biol. Lett., 2018, 14, 20190262.
[Non-Patent Literature 7] J. G. Millar et al., Semiochemicals in Pest and Weed Control, 2005, Chapter 2, 11-27.
[Non-Patent Literature 8] J. G. Millar et al., Nat. Prod. Rep., 2015, 32, 1067.
[Non-Patent Literature 9] J. Brecher, Pure Appl. Chem., 2006, 78, 1897-1970.
[Non-Patent Literature 10] I. Ohtani et al., J. Am. Chem. Soc., 1991, 113, 4092-4096.

PROBLEMS TO BE SOLVED BY THE INVENTION

However, the process described in Non-Patent Literature 1 is not efficient, because the process requires a step of subjecting (1RS,3SR,4SR)-ethyl 3-hydroxy-4,5,5-trimethylcyclopentane-1-carboxylate to a kinetic resolution reaction with a lipase in the presence of vinyl acetate to obtain both enantiomers, and then five steps for obtaining (1R,4R)-α-necrodyl isobutyrate and (1S,4S)-α-necrodyl isobutyrate from each of the enantiomers. The five steps comprise a step of isomerizing an exo-olefin into a trisubstituted olefin using metallic lithium in ethylenediamine. It is difficult to stop this reaction at a proper timing. If this reaction is continued for a too long period of time, an undesired tetra-substituted olefin forms, possibly resulting in a decrease in yield. Non-Patent Literature 1 does not describe experimental procedures for each of the enantiomers, and thus their exact yields are unknown. An overall yield of the five steps of preparing (1R,4R)-α-necrodyl isobutyrate and (1S,4S)-α-necrodyl isobutyrate from the compounds obtained in the kinetic resolution reaction is estimated to be 39% or lower, from the description of the experimental section on the racemate synthesis.

In the process described in Non-Patent Literature 2, an essential oil of *Lavandula luisieri* is purified by distillation to obtain trans-α-necrodyl acetate, which ester is subjected to a solvolysis reaction, double bond migration using a boron trifluoride-ethyl ether complex, and acylation of the alcohol moiety to obtain γ-necrodyl isobutyrate, which compound is then identified as a sex pheromone of spherical mealybug. Non-Patent Literature 2 describes that trans-α- necrodol was analyzed under conditions where possible two-enantiomers would be separated, and only a single enantiomer peak was detected. It is not clarified which enantiomer this single enantiomer is among the two enantiomers. In other words, an absolute configuration of γ-necrodyl isobutyrate, which is a sex pheromone of spherical mealybug, remains unknown.

In some insects, an isomer of their sex pheromones may have an attraction inhibitory activity. Thus, such an impurity may impair the function of a sex pheromone such as the attracting activity of pheromone-based trap. Therefore, determination of the absolute configuration of natural products is essential to use sex pheromones for detecting and monitoring pests of interest.

SUMMARY OF THE INVENTION

The present invention has been made in these circumstances, and aims to provide processes each for efficiently preparing optically active trans-α-necrodyl isobutyrate and γ-necrodyl isobutyrate in a high yield and a high purity. It is possible to determine the absolute configuration of a sex pheromone of spherical mealybug by bioactivity tests using the optically active γ-necrodyl isobutyrate.

As a result of the intensive researches, the present inventors have found that a (1S,2R)-(2-hydroxy-3,5,5-trimethyl-3-cyclopentenyl)methyl carboxylate compound and a (1R,2S)-(2-acetoxy-3,5,5-trimethyl-3-cyclopentenyl)methyl carboxylate compound are each prepared in 99% ee (enantiomeric excess) or more by subjecting a (1RS,2SR)-(2-hydroxy-3,5,5-trimethyl-3-cyclopentenyl)methyl carboxylate compound to a kinetic resolution reaction with a lipase in the presence of vinyl acetate, and thus have completed the present invention.

The present inventors also have successfully prepared (1R,4R)-α-necrodyl isobutyrate, i.e., (1R,4R)-(3,4,5,5-tetramethyl-2-cyclopentenyl)methyl isobutyrate (overall yield 88%) and (1S,4S)-α-necrodyl isobutyrate, i.e., (1S,4S)-(3,4,5,5-tetramethyl-2-cyclopentenyl)methyl isobutyrate (overall yield 76%) in three steps from the two carboxylate compounds obtained, and thus have completed the present invention. The overall yield, 88%, of (1R,4R)-(3,4,5,5-tetramethyl-2-cyclopentenyl)methyl isobutyrate is calculated by multiplication of the yields in Examples 3, 4, and 5 described below, and the overall yield, 76%, of (1S,4S)-(3,4,5,5-tetramethyl-2-cyclopentenyl)methyl isobutyrate is calculated by multiplication of the yields in Examples 8, 9, and 10 described below.

The present inventors further have successfully prepared (R)-γ-necrodyl isobutyrate, i.e., (R)-(2,2,3,4-tetramethyl-3-cyclopentenyl)methyl isobutyrate and (S)-γ-necrodyl isobutyrate, i.e., (S)-(2,2,3,4-tetramethyl-3-cyclopentenyl)methyl isobutyrate by subjecting the two α-necrodyl isobutyrate compounds thus obtained, respectively, to a double bond migration reaction, and thus have completed the present invention.

According to one aspect of the present invention, the present invention provides a process for preparing a (1S,2R)-(2-hydroxy-3,5,5-trimethyl-3-cyclopentenyl)methyl carboxylate compound of the following general formula (S,R)-(2):

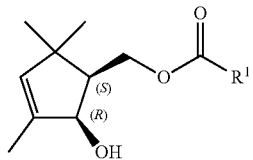

(S,R)-(2)

wherein R¹ represents a monovalent hydrocarbon group having 1 to 6 carbon atoms, and
a bold wedged bond represents the absolute configuration, and
a (1R,2S)-(2-acetoxy-3,5,5-trimethyl-3-cyclopentenyl)methyl carboxylate compound of the following general formula (R,S)-(3):

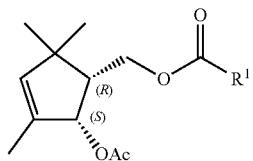

(R,S)-(3)

wherein R¹ is as defined above, a hashed wedged bond represents the absolute configuration, and Ac represents an acetyl group,
the process comprising:
subjecting a (1RS,2SR)-(2-hydroxy-3,5,5-trimethyl-3-cyclopentenyl)methyl carboxylate compound of the following general formula (RS,SR)-(2):

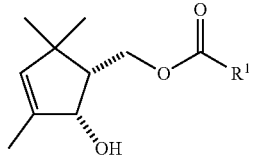

(RS,SR)-(2)

wherein R¹ is as defined above, and a hashed unwedged bond represents a relative configuration,
to a kinetic resolution reaction with a lipase in the presence of vinyl acetate to obtain the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)).

According to another aspect of the present invention, the present invention provides a process for preparing (1R,4R)-(3,4,5,5-tetramethyl-2-cyclopentenyl)methyl isobutyrate of the following formula (R,R)-(5):

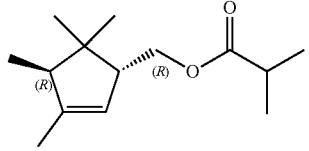

(R,R)-(5)

wherein a hashed wedged bond and a bold wedged bond represent the absolute configuration, the process comprising:

the aforesaid process for preparing the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)), and subjecting the (1R,2S)-(2-acetoxy-3,5,5-trimethyl-3-cyclopentenyl)methyl carboxylate compound ((R,S)-(3)) thus obtained to a solvolysis reaction or a reduction reaction to form (1R,2S)-(2-hydroxy-3,5,5-trimethyl-3-cyclopentenyl)methanol of the following formula (R,S)-(1):

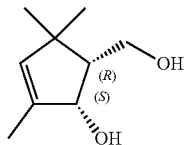
(R,S)-(1)

wherein a hashed wedged bond represents the absolute configuration, subjecting (1R,2S)-(2-hydroxy-3,5,5-trimethyl-3-cyclopentenyl)methanol ((R,S)-(1)) thus obtained to an isobutyrylation reaction to form (1R,2S)-(3,5,5-trimethyl-2-isobutyryloxy-3-cyclopentenyl)methyl isobutyrate of the following formula (R,S)-(4):

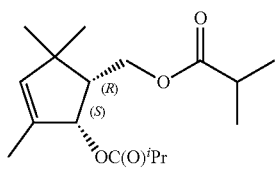
(R,S)-(4)

wherein a hashed wedged bond represents the absolute configuration, and $^i$Pr represents an isopropyl group, and subjecting (1R,2S)-(3,5,5-trimethyl-2-isobutyryloxy-3-cyclopentenyl)methyl isobutyrate ((R,S)-(4)) thus obtained to a nucleophilic substitution reaction with a methylating agent (8) of the following general formula (8):

$$CH_3-M \quad (8)$$

wherein M represents Li, MgZ$^1$, ZnZ$^1$, Cu, CuZ$^1$, or CuLiZ$^1$, wherein Z$^1$ represents a halogen atom or a methyl group, to form (1R,4R)-(3,4,5,5-tetramethyl-2-cyclopentenyl)methyl isobutyrate ((R,R)-(5)).

According to another aspect of the present invention, the present invention provides for a process preparing (R)-(2,2,3,4-tetramethyl-3-cyclopentenyl)methyl isobutyrate of the following formula (R)-(6):

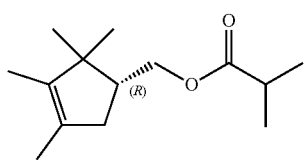
(R)-(6)

wherein a hashed wedged bond represents the absolute configuration, the process comprising:

the aforesaid process for preparing (1R,4R)-(3,4,5,5-tetramethyl-2-cyclopentenyl)methyl isobutyrate ((R,R)-(5)), and subjecting (1R,4R)-(3,4,5,5-tetramethyl-2-cyclopentenyl)methyl isobutyrate ((R,R)-(5)) thus obtained to a double bond migration reaction to form (R)-(2,2,3,4-tetramethyl-3-cyclopentenyl)methyl isobutyrate ((R)-(6)).

According to another aspect of the present invention, the present invention provides a process for preparing (1S,4S)-(3,4,5,5-tetramethyl-2-cyclopentenyl)methyl isobutyrate of the following formula (S,S)-(5):

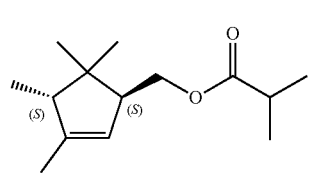
(S,S)-(5)

wherein a hashed wedged bond and a bold wedged bond represent the absolute configuration, the process comprising:

the aforesaid process for preparing the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)), and subjecting the (1S,2R)-(2-hydroxy-3,5,5-trimethyl-3-cyclopentenyl)methyl carboxylate compound ((S,R)-(2)) thus obtained to a solvolysis reaction or a reduction reaction to form (1S,2R)-(2-hydroxy-3,5,5-trimethyl-3-cyclopentenyl)methanol of the following formula (S,R)-(1):

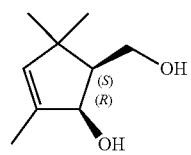
(S,R)-(1)

wherein a bold wedged bond represents the absolute configuration, subjecting (1S,2R)-(2-hydroxy-3,5,5-trimethyl-3-cyclopentenyl)methanol ((S,R)-(1)) thus obtained to an isobutyrylation reaction to form (1S,2R)-(3,5,5-trimethyl-2-isobutyryloxy-3-cyclopentenyl)methyl isobutyrate of the following formula (S,R)-(4):

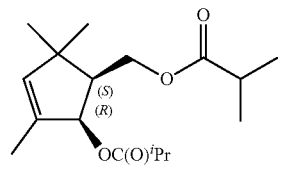
(S,R)-(4)

wherein a bold wedged bond represents the absolute configuration, and $^i$Pr represents an isopropyl group, and subjecting (1S,2R)-(3,5,5-trimethyl-2-isobutyryloxy-3-cyclopentenyl)methyl isobutyrate ((S,R)-(4)) thus obtained to a nucleophilic substitution reaction with a methylating agent (8) of the following general formula (8):

$$CH_3-M \quad (8)$$

wherein M represents Li, MgZ¹, ZnZ¹, Cu, CuZ¹, or CuLiZ¹, wherein Z¹ represents a halogen atom or a methyl group
to form (1S,4S)-(3,4,5,5-tetramethyl-2-cyclopentenyl) methyl isobutyrate ((S,S)-(5)).

According to another aspect of the present invention, the present invention provides a process for preparing (S)-(2,2, 3,4-tetramethyl-3-cyclopentenyl)methyl isobutyrate of the following formula (S)-(6):

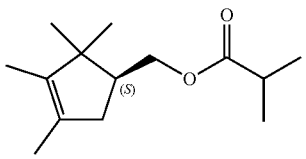

(S)-(6)

wherein a bold wedged bond represents the absolute configuration,
the process comprising:
the aforesaid process for preparing (1S,4S)-(3,4,5,5-tetramethyl-2-cyclopentenyl)methyl isobutyrate ((S,S)-(5)), and
subjecting (1S,4S)-(3,4,5,5-tetramethyl-2-cyclopentenyl) methyl isobutyrate ((S,S)-(5)) thus obtained to a double bond migration reaction to form (S)-(2,2,3,4-tetramethyl-3-cyclopentenyl)methyl isobutyrate ((S)-(6)).

According to the present invention, it is possible to prepare a (1S,2R)-(2-hydroxy-3,5,5-trimethyl-3-cyclopentenyl)methyl carboxylate compound and a (1R,2S)-(2-acetoxy-3,5,5-trimethyl-3-cyclopentenyl)methyl carboxylate compound in both 99% ee or more, and optically active trans-α-necrodyl isobutyrate and γ-necrodyl isobutyrate may be prepared from the aforesaid compounds efficiently in a high yield and a high purity. Moreover, it is also possible to determine the absolute configuration of a sex pheromone of spherical mealybug by bioactivity tests using the optically active γ-necrodyl isobutyrate.

DETAILED DESCRIPTION OF THE PREFERRED EMBODIMENTS

Embodiments of the present invention will be described in detail below. It should be noted that the present invention is not limited to or by the embodiments.

A hashed unwedged bond indicating a relative configuration and a hashed wedged bond and a bold wedged bond both indicating the absolute configuration in the present specification are in accordance with Non-Patent Literature 9 listed above.

A. trans-α-Necrodyl isobutyrate and γ-necrodyl isobutyrate that are prepared in a process according to the present invention will be described below.
(a) trans-α-Necrodyl isobutyrate The term "α-necrodyl compound" refers to a group of compounds having a (3,4,5,5-tetramethyl-2-cyclopentenyl) methyl group. The term "trans-α-necrodyl compound" refers to a group of compounds wherein the substituent at position 1 and the methyl group at position 4 in the α-necrodyl compound are made in a trans configuration.

A target compound in the present invention is optically active trans-α-necrodyl isobutyrate among α-necrodyl compounds. Optically active trans-α-necrodyl isobutyrate includes (1R,4R)-(3,4,5,5-tetramethyl-2-cyclopentenyl) methyl isobutyrate of the following formula (R,R)-(5) and (1S,4S)-(3,4,5,5-tetramethyl-2-cyclopentenyl)methyl isobutyrate of the following formula (S,S)-(5).

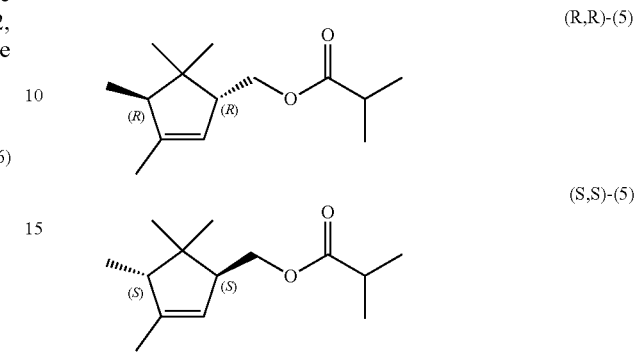

The bold wedged bonds and the hashed wedged bonds in the formulae (R,R)-(5) and (S,S)-(5) represent the absolute configuration.
(b) γ-Necrodyl isobutyrate The term "γ-necrodyl compound" refers to a group of compounds having a (2,2,3,4-tetramethyl-3-cyclopentenyl) methyl group.

A target compound in the present invention is optically active γ-necrodyl isobutyrate among γ-necrodyl compounds. Optically active γ-Necrodyl isobutyrate includes (R)-(2,2,3, 4-tetramethyl-3-cyclopentenyl)methyl isobutyrate of the following formula (R)-(6) and (S)-(2,2,3,4-tetramethyl-3-cyclopentenyl)methyl isobutyrate of the following formula (S)-(6).

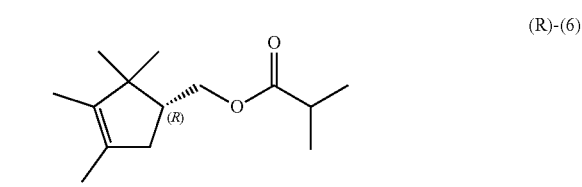

The bold wedged bond and the hashed wedged bond in the formulae (R)-(6) and (S)-(6) represent the absolute configuration.

B. Next, processes for preparing optically active trans-α-necrodyl isobutyrate and γ-necrodyl isobutyrate according to the present invention will be described below.

The present inventors have investigated a plan for synthesis of optically active trans-α-necrodyl isobutyrate ((R, R)-(5) and (S,S)-(5)) and γ-necrodyl isobutyrate ((R)-(6) and (S)-(6)), as described below.

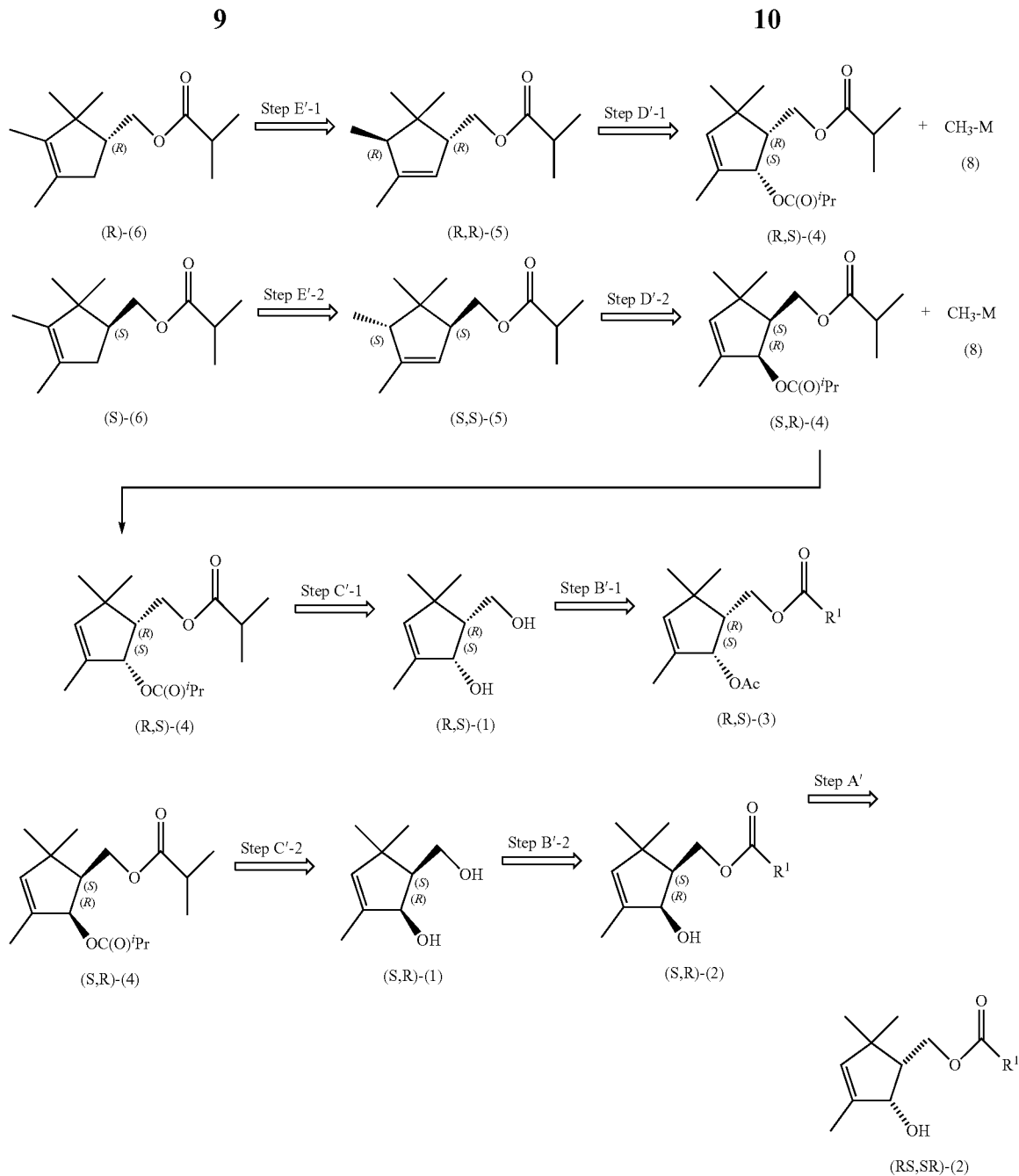

In the reaction formulae of the retrosynthetic analysis shown above, the open arrows represent transforms in the retrosynthetic analysis. $R^1$ represents a monovalent hydrocarbon group having 1 to 6 carbon atoms, $^i$Pr represents an isopropyl group, Ac represents an acetyl group, and M represents a cationic moiety (partial structure excluding the methyl group in a methylating agent described below). The bold wedged bonds and the hashed wedged bonds in the formulae (R)-(6), (S)-(6), (R,R)-(5), (S,S)-(5), (R,S)-(4), (S,R)-(4), (R,S)-(1), (S,R)-(1), (R,S)-(3), and (S,R)-(2) represent the absolute configuration, and the hashed unwedged bonds in the formula (RS,SR)-(2) represent a relative configuration.

The steps will be described below.

Step E'-1 A target compound (R)-(2,2,3,4-tetramethyl-3-cyclopentenyl)methyl isobutyrate ((R)-(6)) is thought to be synthesized via double bond migration in (1R,4R)-(3,4,5,5-tetramethyl-2-cyclopentenyl)methyl isobutyrate ((R,R)-(5)) in the reaction formula. This is because the tetrasubstituted double bond is probably more stable than the trisubstituted double bond.

Step E'-2 A target compound (S)-(2,2,3,4-tetramethyl-3-cyclopentenyl)methyl isobutyrate ((S)-(6)) is thought to be synthesized via double bond migration in (1S,4S)-(3,4,5,5-tetramethyl-2-cyclopentenyl)methyl isobutyrate ((S,S)-(5)) in the reaction formula. This is because the tetrasubstituted double bond is probably more stable than the trisubstituted double bond.

Step D'-1 A target compound (1R,4R)-(3,4,5,5-tetramethyl-2-cyclopentenyl)methyl isobutyrate ((R,R)-(5)) is thought to be synthesized via a regio- and stereoselective nucleophilic substitution reaction between (1R,2S)-(3,5,5-trimethyl-2- isobutyryloxy-3-cyclopentenyl)methyl isobutyrate ((R,S)-(4)) in the reaction formula and a methylating agent (8) in the reaction formula.
Step D'-2 A target compound (1S,4S)-(3,4,5,5-tetramethyl-2-cyclopentenyl)methyl isobutyrate ((S,S)-(5)) is thought to be synthesized via a regio- and stereoselective nucleophilic substitution reaction between (1S,2R)-(3,5,5-trimethyl-2-isobutyryloxy-3-cyclopentenyl)methyl isobutyrate ((S,R)-(4)) in the reaction formula and a methylating agent (8) in the reaction formula.
Step C'-1 A target compound (1R,2S)-(3,5,5-trimethyl-2-isobutyryloxy-3-cyclopentenyl)methyl isobutyrate ((R,S)-(4)) is thought to be synthesized by subjecting (1R,2S)-(2-hydroxy-3,5,5-trimethyl-3-cyclopentenyl)methanol ((R,S)-(1)) in the reaction formula to an isobutyrylation reaction.
Step C'-2 A target compound (1S,2R)-(3,5,5-trimethyl-2-isobutyryloxy-3-cyclopentenyl)methyl isobutyrate ((S,R)-(4)) is thought to be synthesized by subjecting (1S,2R)-(2-hydroxy-3,5,5-trimethyl-3-cyclopentenyl)methanol ((S,R)-(1)) in the reaction formula to an isobutyrylation reaction.
Step B'-1 A target compound (1R,2S)-(2-hydroxy-3,5,5-trimethyl-3-cyclopentenyl)methanol ((R,S)-(1)) is thought to be synthesized by subjecting a (1R,2S)-(2-acetoxy-3,5,5-trimethyl-3-cyclopentenyl)methyl carboxylate compound ((R,S)-(3)) in the reaction formula to a solvolysis reaction or a reduction reaction.
Step B'-2 A target compound (1S,2R)-(2-hydroxy-3,5,5-trimethyl-3-cyclopentenyl)methanol ((S,R)-(1)) is thought to be synthesized by subjecting a (1S,2R)-(2-hydroxy-3,5,5-trimethyl-3-cyclopentenyl)methyl carboxylate compound ((S,R)-(2)) in the reaction formula to a solvolysis reaction or a reduction reaction.
Step A' Target compounds, (1R,2S)-(2-acetoxy-3,5,5-trimethyl-3-cyclopentenyl)methyl carboxylate compound ((R,S)-(3)) and (1S,2R)-(2-hydroxy-3,5,5-trimethyl-3-cyclopentenyl)methyl carboxylate compound ((S,R)-(2)), are thought to be synthesized by subjecting a (1RS,2SR)-(2-hydroxy-3,5,5-trimethyl-3-cyclopentenyl)methyl carboxylate compound ((RS,SR)-(2)) in the reaction formula to a kinetic resolution reaction with a lipase in the presence of vinyl acetate.

In consideration of the retrosynthetic analysis, the reaction scheme according to an embodiment of the present invention is as shown below:

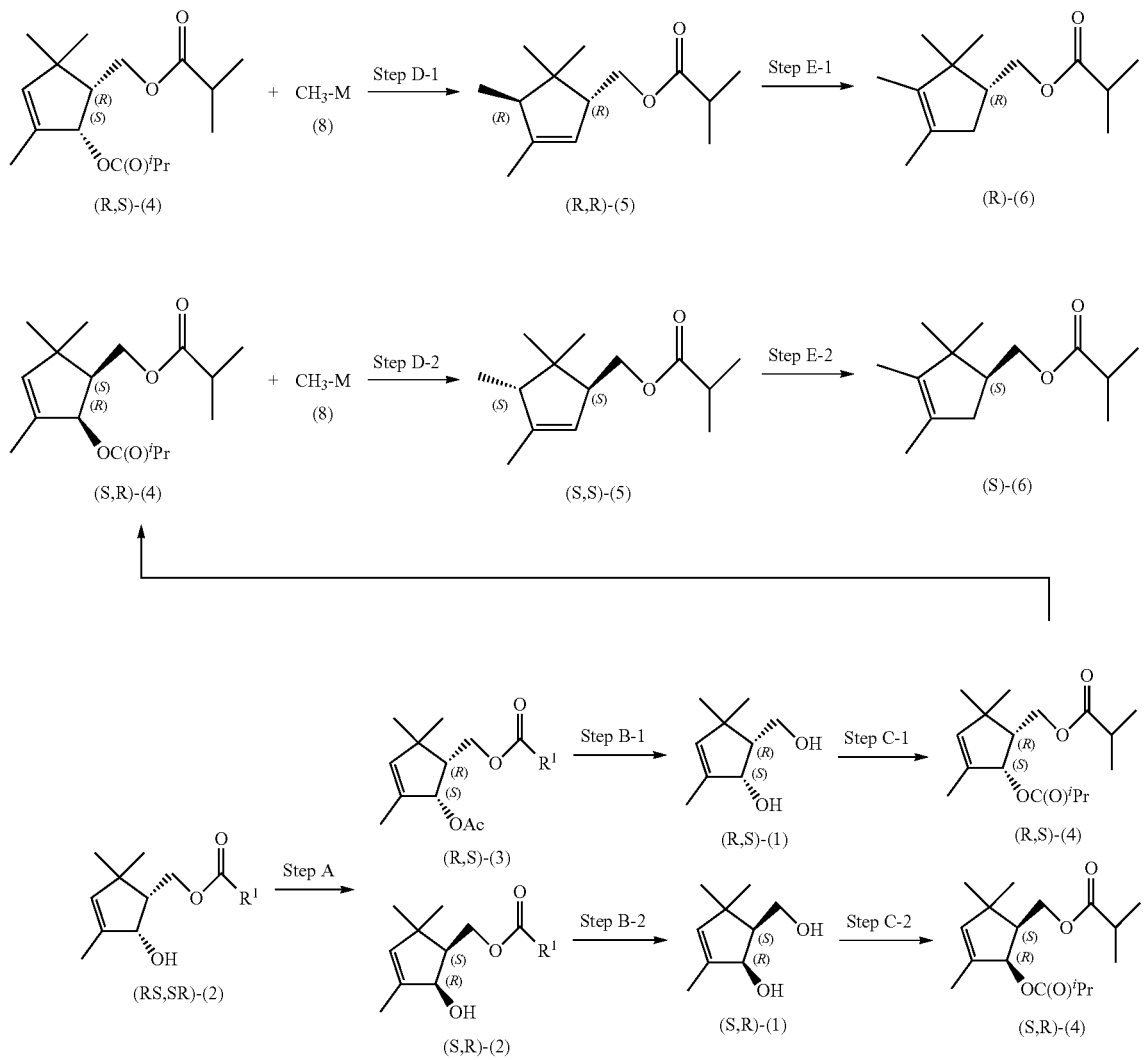

The absolute configuration is confirmed by, as shown in the following reaction formulae, converting (1R,4R)-(3,4,5,5-tetramethyl-2-cyclopentenyl)methyl isobutyrate ((R,R)-(5)) into (1R,4R)-(3,4,5,5-tetramethyl-2-cyclopentenyl)methanol ((R,R)-(7)) having the known absolute configuration (step F-1 shown below) and converting (1S,4S)-(3,4,5,5-tetramethyl-2-cyclopentenyl)methyl isobutyrate ((S,S)-(5)) into (1S,4S)-(3,4,5,5-tetramethyl-2-cyclopentenyl)methanol ((S,S)-(7)) having the known absolute configuration (step F-2 shown below) (see Examples 6 and 11), and comparing the GC retention times of (1R,4R)-(3,4,5,5-tetramethyl-2-cyclopentenyl)methanol ((R,R)-(7)) and (1S,4S)-(3,4,5,5-tetramethyl-2-cyclopentenyl)methanol ((S,S)-(7)) with those of (1R,4R)-(3,4,5,5-tetramethyl-2-cyclopentenyl)methanol ((R,R)-(7)) and (1S,4S)-(3,4,5,5-tetramethyl-2-cyclopentenyl)methanol ((S,S)-(7)) described in Non-Patent Literature 1 listed above.

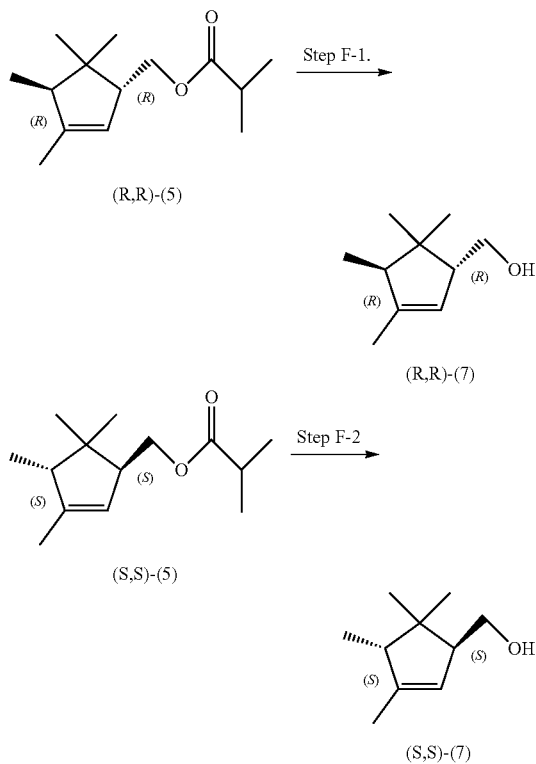

The bold wedged bonds and the hashed wedged bonds in the formulae (R,R)-(5), (S,S)-(5), (R,R)-(7), and (S,S)-(7) represent the absolute configurations.

The absolute configuration is further confirmed by the Mosher method wherein the (1S,2R)-(2-hydroxy-3,5,5-trimethyl-3-cyclopentenyl)methyl carboxylate compound ((S,R)-(2)) is reacted with a Mosher's reagent (α-methoxy-α-(trifluoromethyl)phenylacetyl chloride) to give an MTPA ester (Non-Patent Literature 10).

The steps A to F, which are embodiments of the present invention, will be described in detail below.

[1] Step A

Step A to synthesize the (1R,2S)-(2-acetoxy-3,5,5-trimethyl-3-cyclopentenyl)methyl carboxylate compound ((R,S)-(3)) and the (1S,2R)-(2-hydroxy-3,5,5-trimethyl-3-cyclopentenyl)methyl carboxylate compound ((S,R)-(2)) will be described below. The (1R,2S)-(2-acetoxy-3,5,5-trimethyl-3-cyclopentenyl)methyl carboxylate compound ((R,S)-(3)) and the (1S,2R)-(2-hydroxy-3,5,5-trimethyl-3-cyclopentenyl)methyl carboxylate compound ((S,R)-(2)) are synthesized by subjecting the (1RS,2SR)-(2-hydroxy-3,5,5-trimethyl-3-cyclopentenyl)methyl carboxylate compound ((RS,SR)-(2)) to a kinetic resolution reaction with a lipase in the presence of vinyl acetate, if necessary, in a solvent, as shown in the following chemical reaction formula:

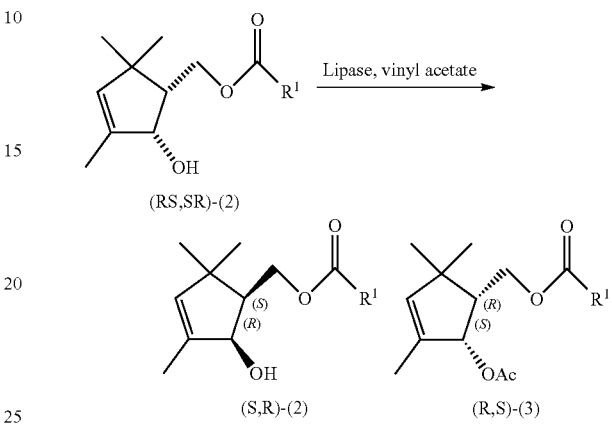

The hashed unwedged bonds in the general formula (RS,SR)-(2) represent a relative configuration, and the bold wedged bonds in the general formula (S,R)-(2) and the hashed wedged bonds in the general formula (R,S)-(3) represent the absolute configuration, and Ac in the general formula (R,S)-(3) represents an acetyl group.

$R^1$ in the general formulae (RS,SR)-(2), (S,R)-(2), and (R,S)-(3) represent a monovalent hydrocarbon group having 1 to 6, preferably 3 to 5 carbon atoms.

Examples of the monovalent hydrocarbon group include linear saturated hydrocarbon groups such as a methyl group, an ethyl group, an n-propyl group, an n-butyl group, an n-pentyl group, and an n-hexyl group; branched saturated hydrocarbon groups such as an isopropyl group, a 2-methylbutyl group, and a t-butyl group; cyclic saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group; and isomers thereof. A part of the hydrogen atoms in the hydrocarbon group may be substituted with a monovalent hydrocarbon group having 1 to 5 carbon atoms.

$R^1$ is preferably a branched saturated hydrocarbon group, which is a bulky group, such as an isopropyl group, a 2-methylbutyl group, or a t-butyl group, more preferably, a t-butyl group, in view of the easy preparation of the (1RS,2SR)-(2-hydroxy-3,5,5-trimethyl-3-cyclopentenyl)methyl carboxylate compound ((RS,SR)-(2)).

The (1RS,2SR)-(2-hydroxy-3,5,5-trimethyl-3-cyclopentenyl)methyl carboxylate compound ((RS,SR)-(2)) is a racemate that is an equivalent mixture of a (1R,2S)-(2-hydroxy-3,5,5-trimethyl-3-cyclopentenyl)methyl carboxylate compound of the following general formula (R,S)-(2) and a (1S,2R)-(2-hydroxy-3,5,5-trimethyl-3-cyclopentenyl) methyl carboxylate compound of the following general formula (S,R)-(2), or an enantiomeric mixture containing enantiomers in any proportions.

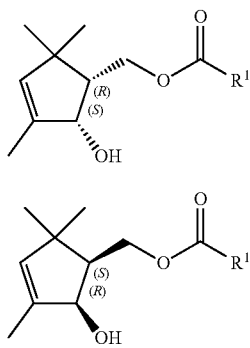

(R,S)-(2)

(S,R)-(2)

The hashed wedged bonds in the general formula (R,S)-(2) and the bold wedged bonds in the general formula (S,R)-(2) represent the absolute configuration.

Specific examples of the (1RS,2SR)-(2-hydroxy-3,5,5-trimethyl-3-cyclopentenyl)methyl carboxylate compound ((1RS,2SR)-(2)) include (1RS,2SR)-(2-hydroxy-3,5,5-trimethyl-3-cyclopentenyl)methyl acetate, (1RS,2SR)-(2-hydroxy-3,5,5-trimethyl-3-cyclopentenyl)methyl propionate, (1RS,2SR)-(2-hydroxy-3,5,5-trimethyl-3-cyclopentenyl) methyl pivalate ((RS,SR)-(2A)), and (1RS,2SR)-(2-hydroxy-3,5,5-trimethyl-3-cyclopentenyl)methyl benzoate. (1RS,2SR)-(2-Hydroxy-3,5,5-trimethyl-3-cyclopentenyl)methyl pivalate ((RS,SR)-(2A)) is preferred in view of the ease of the preparation of the (1RS,2SR)-(2-hydroxy-3,5,5-trimethyl-3-cyclopentenyl)methyl carboxylate compound (see Example 1 below).

(1RS,2SR)-(2-Hydroxy-3,5,5-trimethyl-3-cyclopentenyl)methyl carboxylate compound ((RS,SR)-(2)) may be prepared, for example, by selectively esterifying the primary alcohol of (1RS,2SR)-(2-hydroxy-3,5,5-trimethyl-3-cyclopentenyl)methanol ((RS,SR)-(1)).

The lipase that may be used in the kinetic resolution reaction may be any lipase that functions as a catalyst which shows sufficient difference between a rate of the reaction of one enantiomer with vinyl acetate and a rate of the reaction of the other enantiomer with vinyl acetate. Examples of the lipase include lipases produced in microorganisms belonging to at least one selected from the genera *Aspergillus, Burkholderia, Candida*, and *Pseudomonas*. For example, the genus *Aspergillus* includes *Aspergillus niger*; the genus *Burkholderia* includes *Burkholderia cepacia*; the genus *Candida* includes *Candida antarctica*; and the genus *Pseudomonas* includes *Pseudomonas fluorescens*. A lipase derived from *Pseudomonas fluorescens* is preferred in view of the reactivity. The lipase may be used in a form of a microorganism, a fungus body, an enzyme, or an enzyme immobilized on an insoluble carrier such as a synthetic resin and/or mineral. Such lipases may be commercially available one or may be prepared in house. Preferred commercially available products include Lipase AK Amano (FUJIFILM Wako Pure Chemical Corporation).

An amount of the lipase in enzyme unit U, which is a unit to represent an enzyme's activity, is preferably from 200 to 200,000 U, more preferably 2,000 to 100,000 U, even more preferably 10,000 to 50,000 U, per gram of the substrate, (1RS,2SR)-(2-hydroxy-3,5,5-trimethyl-3-cyclopentenyl)methyl carboxylate compound ((RS,SR)-(2)), in view of the reaction rate and/or enzyme stability.

An amount of vinyl acetate used in the kinetic resolution reaction with lipase is preferably from 0.5 to 100 mol, more preferably 0.5 to 10 mol, even more preferably 0.5 to 3.0 mol, per mol of the substrate, (1RS,2SR)-(2-hydroxy-3,5,5-trimethyl-3-cyclopentenyl)methyl carboxylate compound ((RS,SR)-(2)), in view of the reactivity and reaction rate.

The solvent to be used in the kinetic resolution reaction with lipase may be vinyl acetate itself, or may be one or more solvents selected from the group consisting of ether solvents such as tetrahydrofuran, 4-methyltetrahydropyran, t-butyl methyl ether, and 1,4-dioxane; hydrocarbon solvents such as toluene, xylene, and hexane; alcohol solvents such as methanol, ethanol, and isopropyl alcohol; and polar solvents such as dimethylsulfoxide, N,N-dimethylformamide, and acetonitrile. Ether solvents such as tetrahydrofuran, 4-methyltetrahydropyran, t-butyl methyl ether, and 1,4-dioxane; and hydrocarbon solvents such as toluene, xylene, and hexane are preferred in view of the catalytic activity and stability of the enzyme.

The solvent may be used either alone or in combination thereof, if necessary. When vinyl acetate acts also as a solvent, any additional solvent other than vinyl acetate may not be incorporated. The solvent may be commercially available one.

An amount of the solvent used is preferably from 0 to 200,000 mL, more preferably 0 to 20,000 mL, even more preferably 0 to 10,000 mL, per mol of the substrate, (1RS,2SR)-(2-hydroxy-3,5,5-trimethyl-3-cyclopentenyl)methyl carboxylate compound ((RS,SR)-(2)), in view of the reaction rate and/or enzyme stability.

An optimal reaction temperature in the kinetic resolution reaction with a lipase reaction varies, depending on a species of the lipase to be used, and is preferably from 10 to 100° C., more preferably 20 to 80° C., even more preferably 30 to 60° C., in view of the reaction rate and/or enzyme stability.

The reaction time in the kinetic resolution reaction with a lipase varies, depending on a species of the lipase to be used and/or an amount of the reactant and/or a reaction scale, and is preferably from 0.1 to 240 hours, more preferably 1 to 120 hours.

Specific examples of the (1S,2R)-(2-hydroxy-3,5,5-trimethyl-3-cyclopentenyl)methyl carboxylate compound ((S,R)-(2)) include (1S,2R)-(2-hydroxy-3,5,5-trimethyl-3-cyclopentenyl)methyl acetate, (1S,2R)-(2-hydroxy-3,5,5-trimethyl-3-cyclopentenyl)methyl propionate, (1S,2R)-(2-hydroxy-3,5,5-trimethyl-3-cyclopentenyl)methyl pivalate ((S,R)-(2A)), and (1S,2R)-(2-hydroxy-3,5,5-trimethyl-3-cyclopentenyl)methyl benzoate. (1S,2R)-(2-Hydroxy-3,5,5-trimethyl-3-cyclopentenyl)methyl pivalate ((S,R)-(2A)) is preferred in view of the ease of preparation of (1RS,2SR)-(2-hydroxy-3,5,5-trimethyl-3-cyclopentenyl)methyl carboxylate compound ((RS,SR)-(2)) (see Example 2 below).

Specific examples of the (1R,2S)-(2-acetoxy-3,5,5-trimethyl-3-cyclopentenyl)methyl carboxylate compound ((R,S)-(3)) include (1R,2S)-(2-acetoxy-3,5,5-trimethyl-3-cyclopentenyl)methyl acetate, (1R,2S)-(2-acetoxy-3,5,5-trimethyl-3-cyclopentenyl)methyl propionate, (1R,2S)-(2-acetoxy-3,5,5-trimethyl-3-cyclopentenyl)methyl pivalate ((R,S)-(3A)), and (1R,2S)-(2-acetoxy-3,5,5-trimethyl-3-cyclopentenyl)methyl benzoate. (1R,2S)-(2-Acetoxy-3,5,5-trimethyl-3-cyclopentenyl)methyl pivalate ((R,S)-(3A)) is preferred in view of the ease of the preparation of (1RS,2SR)-(2-hydroxy-3,5,5-trimethyl-3-cyclopentenyl)methyl carboxylate compound ((RS,SR)-(2)) (see Example 2 below).

[2] Step B-1 and Step B-2

(1R,2S)-(2-Hydroxy-3,5,5-trimethyl-3-cyclopentenyl)methanol ((R,S)-(1)) is obtained in step B-1, and i (1S,2R)-

(2-hydroxy-3,5,5-trimethyl-3-cyclopentenyl)methanol ((S,R)-(1)) is obtained in step B-2.

(a) First, step B-1 will be described.

In step B-1, (1R,2S)-(2-hydroxy-3,5,5-trimethyl-3-cyclopentenyl)methanol ((R,S)-(1)) may be synthesized by subjecting the (1R,2S)-(2-acetoxy-3,5,5-trimethyl-3-cyclopentenyl)methyl carboxylate compound ((R,S)-(3)) to (i) a solvolysis reaction or (ii) a reduction reaction, as shown in the following chemical reaction formula:

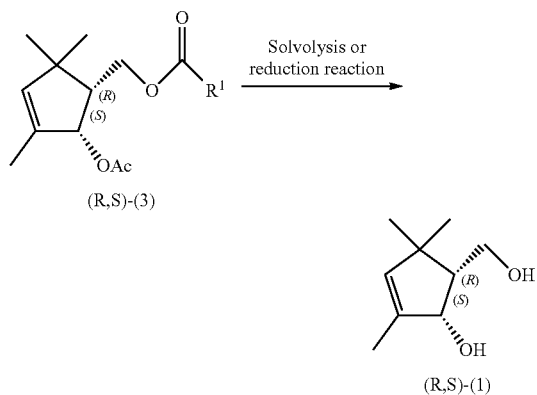

The hashed wedged bonds in the general formulae (R,S)-(3) and (R,S)-(1) represent the absolute configuration.

(i) Solvolysis Reaction

The conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)) may be done by any known solvolysis reaction of an ester. Examples of the solvolysis reaction include a hydrolysis reaction in a solvent in a basic or neutral condition.

Examples of the solvolysis reaction include a hydrolysis reaction in which a reaction substrate is reacted with water in a solvent or with water later added, typically in a solvent in the presence of a base or salt; and an alcoholysis reaction in which a reaction substrate is reacted with alcohol in a solvent. The solvolysis reaction may be carried out with cooling or heating, if necessary.

Examples of the base used in the solvolysis reaction include hydroxide salts such as sodium hydroxide, lithium hydroxide, potassium hydroxide, and barium hydroxide; carbonate salts such as sodium carbonate, potassium carbonate, sodium bicarbonate, and potassium bicarbonate; and metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide.

The base may be used either alone or in combination thereof, if necessary. The base may be commercially available one.

An amount of the base used is preferably from 0.01 to 1000 mol, more preferably 0.1 to 100 mol, even more preferably 0.1 to 10 mol, per mol of the (1R,2S)-(2-acetoxy-3,5,5-trimethyl-3-cyclopentenyl)methyl carboxylate compound ((R,S)-(3)) in view of the reactivity.

Examples of the salts used in the solvolysis include Lewis acids such as aluminum trichloride, aluminum ethoxide, aluminum isopropoxide, aluminum oxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide; and oxides such as alumina, silica gel, and titania.

The salt may be used either alone or in combination thereof, if necessary. The salts may be commercially available 1 one.

An amount of the salts used is preferably from 0.01 to 1000 mol, more preferably 0.1 to 100 mol, even more preferably 0.1 to 10 mol, per mol of the (1R,2S)-(2-acetoxy-3,5,5-trimethyl-3-cyclopentenyl)methyl carboxylate compound ((R,S)-(3)) in view of the reactivity.

Examples of the solvent used in the solvolysis reaction include water; alcohol solvents such as methanol, ethanol, isopropyl alcohol, t-butyl alcohol, benzyl alcohol, methoxyethanol, and ethoxyethanol; ether solvents such as ethylene glycol monomethyl ether, triethylene glycol monomethyl ether, tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform.

The solvent may be used either alone or in combination thereof, if necessary. The solvent may be commercially available one.

An amount of the solvent used varies, depending on a reaction scale, and is preferably from 36 to 200,000 g, more preferably 36 to 20,000 g, even more preferably 36 to 2,000 g, per mol of the (1R,2S)-(2-acetoxy-3,5,5-trimethyl-3-cyclopentenyl)methyl carboxylate compound ((R,S)-(3)) in view of the reactivity and reaction rate.

A reaction temperature in the solvolysis reaction is preferably from −78° C. to a boiling point temperature of a solvent, more preferably −10 to 100° C., in view of the reaction rate and suppression of byproduct formation.

A reaction time of the solvolysis reaction varies, depending on a species of a solvent used and/or a reaction scale, and is preferably from 0.1 to 120 hours.

(ii) Reduction Reaction

The conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)) may be done by any known reduction reaction of an ester. The reduction reaction may be carried out by reacting a reaction substrate with a reducing agent typically in a solvent, with cooling or heating, if needed.

Examples of the reducing agent used in the reduction reaction include hydrogen; boron compounds such as borane, alkylborane, dialkylborane, and bis(3-methyl-2-butyl)borane; metal hydrides such as dialkylsilane, trialkylsilane, monoalkylaluminum hydride, and dialkylaluminum hydride; complex hydrides such as sodium borohydride, lithium borohydride, potassium borohydride, calcium borohydride, sodium aluminum hydride, lithium aluminum hydride, sodium trimethoxy borohydride, zinc borohydride, lithium trimethoxy aluminum hydride, lithium diethoxy aluminum hydride, lithium tri-t-butoxy aluminum hydride, sodium bis(2-methoxyethoxy) aluminum hydride, lithium triethyl borohydride, and diisobutylaluminum hydride; and alkoxy derivatives or alkyl derivatives thereof. The complex hydrides are preferred in view of reaction conditions and/or ease of reaction work-ups.

An amount of the reducing agent used in the reduction reaction varies, depending on a species of a reducing agent and/or reaction conditions to be used, and is preferably from 1 to 500 mol, more preferably 1.8 to 16 mol, per mol of the substrate, (1R,2S)-(2-acetoxy-3,5,5-trimethyl-3-cyclopentenyl)methyl carboxylate compound ((R,S)-(3)).

Examples of a solvent used in the reduction reaction include water; alcohol solvents such as methanol, ethanol, isopropyl alcohol, t-butyl alcohol, benzyl alcohol, methoxyethanol, and ethoxyethanol; ether solvents such as ethylene glycol monomethyl ether, triethylene glycol monomethyl ether, tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform.

The solvent may be used either alone or in combination thereof, if necessary. The solvent may be commercially available one.

The solvent used in the reduction reaction is appropriately selected, depending on a species of a reducing agent to be used. Examples of a preferred combination of the reducing agent and the solvent include a combination of lithium borohydride as the reducing agent with an ether solvent, a mixed solvent of an ether solvent and an alcohol solvent, or a mixed solvent of an ether solvent and a hydrocarbon solvent; and a combination of lithium aluminum hydride as the reducing agent with an ether solvent or a mixed solvent of an ether solvent and a hydrocarbon solvent.

An amount of the solvent used in the reduction reaction varies, depending on a reaction scale, and is preferably from 0.01 to 100,000 g, more preferably 0.1 to 10,000 g, even more preferably 1 to 1,000 g, per mol of the (1R,2S)-(2-acetoxy-3,5,5-trimethyl-3-cyclopentenyl)methyl carboxylate compound ((R,S)-(3)) in view of the reaction rate.

A reaction temperature of the reduction reaction is preferably from −78 to 100° C., more preferably −20 to 80° C., in view of the reaction rate and suppression of byproduct formation.

A reaction time of the reduction reaction varies, depending on a species of a solvent used and/or a reaction scale, and is preferably from 0.1 to 120 hours.

(b) Next, step B-2 will be described.

In step B-2, (1S,2R)-(2-hydroxy-3,5,5-trimethyl-3-cyclopentenyl)methanol ((S,R)-(1)) may be synthesized by subjecting the (1S,2R)-(2-hydroxy-3,5,5-trimethyl-3-cyclopentenyl)methyl carboxylate compound ((S,R)-(2)) to (i) a solvolysis reaction or (ii) a reduction reaction, as shown in the following chemical reaction formula:

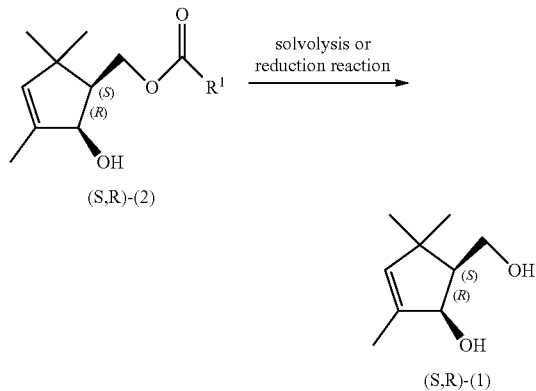

The bold wedged bonds in the general formulae (S,R)-(2) and (S,R)-(1) represent the absolute configuration.

(i) Solvolysis Reaction

The conversion of the (1S,2R)-(2-hydroxy-3,5,5-trimethyl-3-cyclopentenyl)methyl carboxylate compound ((S,R)-(2)) into (1S,2R)-(2-hydroxy-3,5,5-trimethyl-3-cyclopentenyl)methanol ((S,R)-(1)) may be done by any known solvolysis reaction of an ester. Examples of the solvolysis reaction include a hydrolysis reaction in a solvent in a basic or neutral condition.

Examples of the solvolysis reaction include a hydrolysis reaction in which a reaction substrate is reacted with water in a solvent or with water later added, typically in a solvent in the presence of a base or salt: and an alcoholysis reaction in which a reaction substrate is reacted with alcohol in a solvent. The solvolysis reaction may be carried out with cooling or heating, if necessary.

The base used in the solvolysis reaction is as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

An amount of the base used is preferably from 0.01 to 1000 mol, more preferably 0.1 to 100 mol, even more preferably 0.1 to 10 mol, per mol of the (1S,2R)-(2-hydroxy-3,5,5-trimethyl-3-cyclopentenyl)methyl carboxylate compound ((S,R)-(2)) in view of the reactivity.

The salt to be used in the solvolysis reaction is as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

An amount of the salt used is preferably from 0.01 to 1000 mol, more preferably 0.1 to 100 mol, even more preferably 0.1 to 10 mol, per mol of the (1S,2R)-(2-hydroxy-3,5,5-trimethyl-3-cyclopentenyl)methyl carboxylate compound ((S,R)-(2)) in view of the reactivity.

The solvent to be used in the solvolysis reaction is as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

An amount of the solvent used varies, depending on a reaction scale, and is preferably from 18 to 200,000 g, more preferably 18 to 20,000 g, even more preferably 18 to 2,000 g, per mol of the (1S,2R)-(2-hydroxy-3,5,5-trimethyl-3-cyclopentenyl)methyl carboxylate compound ((S,R)-(2)) in view of the reactivity and reaction rate.

The reaction temperature and reaction time in the solvolysis reaction are as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

(ii) Reduction Reaction

The conversion of the (1S,2R)-(2-hydroxy-3,5,5-trimethyl-3-cyclopentenyl)methyl carboxylate compound ((S,R)-(2)) into (1S,2R)-(2-hydroxy-3,5,5-trimethyl-3-cyclopentenyl)methanol ((S,R)-(1)) may be done by any known reduction reaction of an ester. The reduction reaction may be carried out by reacting a reaction substrate with a reducing agent typically in a solvent, with cooling or heating, if needed, The reducing agent in the reduction reaction is as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

An amount of the reducing agent used in the reduction reaction varies, depending on a species of a reducing agent and/or reaction conditions to be used, and is preferably from 1 to 500 mol, more preferably 1.8 to 16 mol, per mol of the substrate, (1S,2R)-(2-hydroxy-3,5,5-trimethyl-3-cyclopentenyl)methyl carboxylate compound ((S,R)-(2)).

The solvent to be used in the reduction reaction is as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

An amount of the solvent used in the reduction reaction varies, depending on a reaction scale, and is preferably from 0.01 to 100,000 g, more preferably 0.1 to 10,000 g, even more preferably 1 to 1,000 g, per mol of the (1S,2R)-(2-hydroxy-3,5,5-trimethyl-3-cyclopentenyl)methyl carboxylate compound ((S,R)-(2)) in view of the reaction rate.

The reaction temperature and reaction time in the reduction reaction are as mentioned for the conversion of the (1R,2S)-(2-acetoxy-3,5,5-trimethyl-3-cyclopentenyl)methyl carboxylate compound ((R,S)-(3)) into (1R,2S)-(2-hydroxy-3,5,5-trimethyl-3-cyclopentenyl)methanol ((R,S)-(1)).

[3] Step C-1 and Step C-2

(1R,2S)-(3,5,5-Trimethyl-2-isobutyryloxy-3-cyclopentenyl)methyl isobutyrate ((R,S)-(4)) is obtained in step C-1, and (1S,2R)-(3,5,5-trimethyl-2-isobutyryloxy-3-cyclopentenyl)methyl isobutyrate ((S,R)-(4)) is obtained in step C-2.

The step for obtaining (1R,2S)-(3,5,5-trimethyl-2-isobutyryloxy-3-cyclopentenyl)methyl isobutyrate ((R,S)-(4)) and the step for obtaining (1S,2R)-(3,5,5-trimethyl-2-isobutyryloxy-3-cyclopentenyl)methyl isobutyrate ((S,R)-(4)) are carried out in the same reaction conditions. Therefore, only step C-1 for synthesizing (1R,2S)-(3,5,5-trimethyl-2-isobutyryloxy-3-cyclopentenyl)methyl isobutyrate ((R,S)-(4)) will be described below. The description is applicable also to step C-2 for synthesizing (1S,2R)-(3,5,5-trimethyl-2-isobutyryloxy-3-cyclopentenyl)methyl isobutyrate ((S,R)-(4)).

(1R,2S)-(3,5,5-Trimethyl-2-isobutyryloxy-3-cyclopentenyl)methyl isobutyrate ((R,S)-(4)) may be synthesized by subjecting (1R,2S)-(2-hydroxy-3,5,5-trimethyl-3-cyclopentenyl)methanol ((R,S)-(1)) to an isobutyrylation reaction, as shown in the following chemical reaction formula:

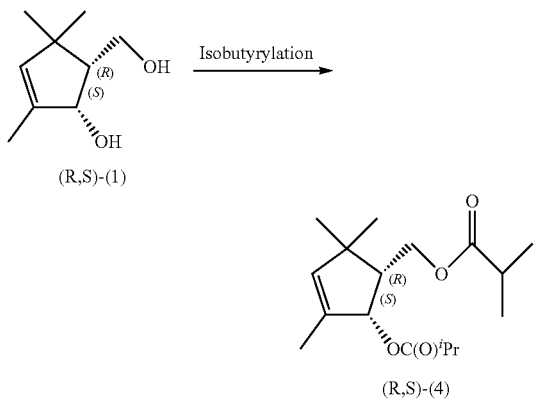

The hashed wedged bonds in the formulae (R,S)-(1) and (R,S)-(4) represent the absolute configuration, and $^i$Pr represents an isopropyl group.

The isobutyrylation reaction may be done in any known process for preparing an ester, for example, (i) a reaction with an acylating agent, (ii) a reaction with a carboxylic acid, and (iii) transesterification.

(i) Reaction with an Acylating Agent

For the reaction with an acylating agent, (1R,2S)-(2-hydroxy-3,5,5-trimethyl-3-cyclopentenyl)methanol ((R,S)-(1)) which is a substrate is sequentially or simultaneously contacted with an acylating agent and a base, typically in a solvent.

Examples of the acylating agent include isobutyryl chloride; isobutyric acid; isobutyric mixed anhydrides such as isobutyric/trifluoroacetic mixed anhydride, isobutyric/methanesulphonic mixed anhydride, isobutyric/trifluoromethanesulfonic mixed anhydride, isobutyric/benzenesulfonic mixed anhydride, and isobutyric/p-toluenesulfonic mixed anhydride; and p-nitrophenyl isobutyrate.

An amount of the acylating agent used is preferably from 2 to 500 mol, more preferably 2 to 50 mol, even more preferably 2 to 5 mol, per mol of the substrate, (1R,2S)-(2-hydroxy-3,5,5-trimethyl-3-cyclopentenyl)methanol ((R,S)-(1)).

Examples of the base used in the reaction with the acylating agent include diisopropylethylamine, N,N-dimethylaniline, N,N-diethylaniline, pyridine, 2-ethyl pyridine, and 4-dimethyl aminopyridine.

An amount of the base used is preferably from 2 to 500 mol, per mol of the substrate, (1R,2S)-(2-hydroxy-3,5,5-trimethyl-3-cyclopentenyl)methanol ((R,S)-(1)).

The solvent used in the reaction with the acylating agent may be the base itself described above, or may be one or more solvents selected from the group consisting of an ether solvent such as tetrahydrofuran, 4-methyltetrahydropyran, diethyl ether, t-butyl methyl ether, or 1,4-dioxane; a hydrocarbon solvent such as toluene, xylene, or hexane; and a polar solvent such as N,N-dimethylformamide, N,N-dimethylacetamide, acetonitrile, dichloromethane, or chloroform.

The solvent may be used either alone or in combination thereof, if necessary. When the base is used as a solvent, any additional solvent other than the base may not be incorporated. The solvent may be commercially available one.

An amount of the solvent used is preferably from 0 to 100,000 g, more preferably 0 to 10,000 g, per mol of the substrate, (1R,2S)-(2-hydroxy-3,5,5-trimethyl-3-cyclopentenyl)methanol ((R,S)-(1)).

When the acylating agent in the reaction is a carboxylic anhydride, a carboxylic mixed anhydride or p-nitrophenyl carboxylate, an acid catalyst may be used instead of the base.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide.

The acylating agent may be used either alone or in combination thereof, if necessary. The acylating agent may be commercially available one.

An amount of the acid catalyst is preferably from 0.0001 to 100 mol in the reaction with the acylating agent such as carboxylic anhydride, carboxylic mixed anhydride, or p-nitrophenyl carboxylate.

A reaction temperature in the reaction with the acylating agent is preferably from −50 to 150° C., more preferably −20 to 50° C., in view of the reaction rate and suppression of by-product formation.

A reaction time of the reaction with the acylating agent varies, depending on a species of a solvent used and/or a reaction scale, and is preferably from 0.1 to 120 hours.

(ii) Reaction with a Carboxylic Acid

The reaction with a carboxylic acid is a dehydration reaction between (1R,2S)-(2-hydroxy-3,5,5-trimethyl-3-cyclopentenyl)methanol ((R,S)-(1)) and a carboxylic acid, and is carried out typically in the presence of an acid catalyst.

Specific examples of the carboxylic acid used in the reaction with (1R,2S)-(2-hydroxy-3,5,5-trimethyl-3-cyclopentenyl)methanol ((R,S)-(1)) include isobutyric acid.

An amount of the carboxylic acid used is preferably from 2 to 500 mol, more preferably 2 to 50 mol, even more preferably 2 to 5 mol, per mol of (1R,2S)-(2-hydroxy-3,5,5-trimethyl-3-cyclopentenyl)methanol ((R,S)-(1)).

An acid catalyst may be used in the reaction between (1R,2S)-(2-hydroxy-3,5,5-trimethyl-3-cyclopentenyl)methanol ((R,S)-(1)) and a carboxylic acid. The acid catalyst may be the acid catalyst mentioned for the reaction with the acylating agent.

An amount of the acid catalyst used is preferably from 0.0001 to 100 mol, more preferably 0.001 to 1 mol, even more preferably 0.01 to 0.05 mol, per mol of (1R,2S)-(2-hydroxy-3,5,5-trimethyl-3-cyclopentenyl)methanol ((R,S)-(1)).

A solvent and an amount of the solvent used in the reaction between (1R,2S)-(2-hydroxy-3,5,5-trimethyl-3-cyclopentenyl)methanol ((R,S)-(1)) and a carboxylic acid may be those mentioned for the reaction with the acylating agent.

A reaction temperature in the reaction of (1R,2S)-(2-hydroxy-3,5,5-trimethyl-3-cyclopentenyl)methanol ((R,S)-(1)) with the carboxylic acid is preferably from −50 to 150° C., more preferably 0 to 150° C., in view of the reaction rate and suppression of by-product formation.

The reaction may be done in a solvent such as a hydrocarbon solvent, such as hexane, heptane, benzene, toluene, xylene, or cumene, while removing the resulting water out of the system by azeotropic distillation. Alternatively, water may be distilled off with refluxing at the boiling point of the solvent in normal pressure, or at a lower temperature than the boiling point of water in a reduced pressure.

A reaction time in the reaction between (1R,2S)-(2-hydroxy-3,5,5-trimethyl-3-cyclopentenyl)methanol ((R,S)-(1)) and the carboxylic acid varies, depending on a species of a solvent used and/or a reaction scale, and is preferably from 0.1 to 120 hours.

(iii) Transesterification

The transesterification reaction is carried out by reacting (1R,2S)-(2-hydroxy-3,5,5-trimethyl-3-cyclopentenyl)methanol ((R,S)-(1)) with an alkyl carboxylate in the presence of an acid catalyst and removing a resulting alcohol.

The alkyl carboxylate is preferably a primary alkyl ester of a carboxylic acid. Methyl carboxylate, ethyl carboxylate, and an n-propyl carboxylate are preferred in view of the cost and/or ease of reaction.

Examples of the carboxylic acid include those mentioned for the reaction with the carboxylic acid.

An amount of the alkyl carboxylate used is preferably from 2 to 500 mol, more preferably 2 to 50 mol, even more preferably 2 to 5 mol, per mol of (1R,2S)-(2-hydroxy-3,5,5-trimethyl-3-cyclopentenyl)methanol ((R,S)-(1)).

Examples of the acid catalyst used in the transesterification reaction include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide.

The acid catalyst may be used either alone or in combination thereof, if necessary. The acid catalyst may be commercially available one.

An amount of the acid catalyst used is preferably from 0.0001 to 100 mol, more preferably 0.001 to 1 mol, even more preferably 0.01 to 0.05 mol, per mol of (1R,2S)-(2-hydroxy-3,5,5-trimethyl-3-cyclopentenyl)methanol ((R,S)-(1)).

The transesterification reaction may be carried out, while the reactant, alkyl carboxylate, works as a solvent, with or without any additional solvent. The embodiment without any additional solvent is preferred, because no extra operation such as concentration or solvent recovery is required.

Examples of the solvent used in the transesterification reaction include ether solvents such as tetrahydrofuran, 4-methyltetrahydropyran, diethyl ether, t-butyl methyl ether, and 1,4-dioxane; and hydrocarbon solvents such as toluene, xylene, and hexane.

The solvent may be used either alone or in combination thereof, if necessary. The solvent may be commercially available 1 one.

An amount of the solvent used is preferably from 10 to 10,000 g, per mol of (1R,2S)-(2-hydroxy-3,5,5-trimethyl-3-cyclopentenyl)methanol ((R,S)-(1)).

The transesterification reaction may be carried out preferably at a temperature near a boiling point of a lower alcohol that is formed in the transesterification, such as C1-C3 alcohol such as methanol, ethanol, and 1-propanol, while distilling the lower alcohol off, in view of the reaction rate. The alcohol may be distilled off at a lower temperature than its boiling point at a reduced pressure.

A reaction time of the transesterification reaction varies, depending on a species of a solvent used and/or a reaction scale, and is preferably from 0.1 to 120 hours.

[4] Step D-1 and Step D-2

(1R,4R)-(3,4,5,5-Tetramethyl-2-cyclopentenyl)methyl isobutyrate ((R,R)-(5)) is obtained in step D-1, and (1S,4S)-(3,4,5,5-tetramethyl-2-cyclopentenyl)methyl isobutyrate ((S,S)-(5)) is obtained in step D-2.

The step for obtaining (1R,4R)-(3,4,5,5-tetramethyl-2-cyclopentenyl)methyl isobutyrate ((R,R)-(5)) and the step for obtaining (1S,4S)-(3,4,5,5-tetramethyl-2-cyclopentenyl) methyl isobutyrate ((S,S)-(5)) may be carried out in the same reaction conditions. Therefore, only step D-1 for synthesizing (1R,4R)-(3,4,5,5-tetramethyl-2-cyclopentenyl)methyl isobutyrate ((R,R)-(5)) will be described below. The description is applicable also to step D-2 for synthesizing (1S,4S)-(3,4,5,5-tetramethyl-2-cyclopentenyl)methyl isobutyrate ((S,S)-(5)).

(1R,4R)-(3,4,5,5-Tetramethyl-2-cyclopentenyl)methyl isobutyrate ((R,R)-(5)) may be synthesized by subjecting the aforesaid (1R,2S)-(3,5,5-trimethyl-2-isobutyryloxy-3-cyclopentenyl)methyl isobutyrate ((R,S)-(4)) to a nucleophilic substitution reaction with a methylating agent, CH$_3$-M (8), as shown in the following chemical reaction formula:

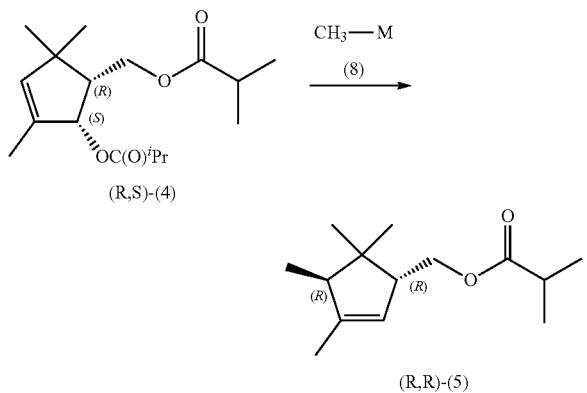

The bold wedged bond and the hashed wedged bonds in the formulae (R,S)-(4) and (R,R)-(5) represent the absolute configuration, and $^i$Pr represents an isopropyl group.

The methylating agent (8) is used in the nucleophilic substitution reaction. An organometal reagent comprising a metal element of Group I or Group II or a transition metal element is typically used in the nucleophilic substitution reaction.

M in the methylating agent (8) represents Li, MgZ$^1$, ZnZ$^1$, Cu, CuZ$^1$, or CuLiZ$^1$, and Z$^1$ represents a halogen atom or a methyl group. Examples of the halogen atom Z$^1$ include a chlorine atom, a bromine atom, and an iodine atom.

The methylating agent (8) is preferably an organolithium reagent, such as methyl lithium; and an organomagnesium reagent, such as a Grignard reagent and a methylmagnesium halide, particularly a Grignard reagent, in view of the selectivity and/or ease of the preparation.

The methylating agent (8) may be prepared in a metal exchange reaction between an organolithium or organomagnesium reagent and at least a stoichiometric amount (1 mol or more) of a transition metal compound in advance, or in-situ where an organolithium or a Grignard reagent and a catalytic amount of a transition metal compound are reacted.

Examples of the transition metal compound include transition metal compounds comprising copper, iron, nickel, palladium, zinc, or silver; cuprous halides, such as copper (I) chloride, copper (I) bromide, and copper (I) iodide; cupric halides, such as copper (II) chloride, copper (II) bromide, and copper (II) iodide; copper cyanides, such as copper (I) cyanide and copper (II) cyanide; copper oxides, such as copper (I) oxide and copper (II) oxide; and copper compounds, such as dilithium tetrachlorocuprate (Li$_2$CuCl$_4$). Copper halides are preferred in view of the reactivity.

An amount of the transition metal compound used is preferably from 0.01 to 10 mol, more preferably 0.1 to 5 mol, per mol of the (1R,2S)-(3,5,5-trimethyl-2-isobutyryloxy-3-cyclopentenyl)methyl isobutyrate ((R,S)-(4)) in view of the reactivity and selectivity.

When the transition metal compound is used in the nucleophilic substitution reaction, a co-catalyst may be incorporated preferably in an amount of 0.01 to 1,000 parts by weight per 100 parts by weight of the transition metal compound to improve the solubility of the transition metal compound in a solvent.

Specific examples of the co-catalyst include phosphorus compounds, such as trialkyl phosphites such as triethyl phosphite, and triarylphosphines such as triphenylphosphine.

In the nucleophilic substitution reaction, a lithium salt such as lithium chloride, lithium bromide, or lithium iodide may be present as a catalyst for the reaction in an amount of 0.001 to 1,000 mol, per mol of (1R,2S)-(3,5,5-trimethyl-2-isobutyryloxy-3-cyclopentenyl)methyl isobutyrate ((R,S)-(4)). A combination of a copper halide and a lithium salt is preferred in view of the reactivity and selectivity.

An amount of the methylating agent (8) used may be properly set, considering a species of the reagents, the reaction conditions, the reaction yield, the economic efficiency including costs of intermediates, and/or ease of isolation and purification of the target compound from the reaction mixture, and is preferably from 0.2 to 100 mol, more preferably 0.5 to 20 mol, even more preferably 0.8 to 5 mol, per mol of (1R,2S)-(3,5,5-trimethyl-2-isobutyryloxy-3-cyclopentenyl)methyl isobutyrate ((R,S)-(4)).

Examples of the solvent used in the nucleophilic substitution reaction include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Tetrahydrofuran is preferred in view of the reactivity and solubility.

The solvent may be used either alone or in combination thereof, if necessary. The solvent may be commercially available one.

An amount of the solvent used varies, depending on a reaction scale, and is preferably from 200 to 4,000 g, per mol of (1R,2S)-(3,5,5-trimethyl-2-isobutyryloxy-3-cyclopentenyl)methyl isobutyrate ((R,S)-(4)) in view of the reaction rate.

A reaction temperature in the preparation of (1R,4R)-(3,4,5,5-tetramethyl-2-cyclopentenyl)methyl isobutyrate ((R,R)-(5)) is preferably from −78 to 150° C., more preferably −78 to 80° C., in view of the reactivity and suppression of by-product formation.

A reaction time in the preparation of (1R,4R)-(3,4,5,5-tetramethyl-2-cyclopentenyl)methyl isobutyrate ((R,R)-(5)) varies, depending on a solvent and/or a reaction scale, and is preferably from 0.1 to 120 hours.

[5] Step E-1 and Step E-2

(R)-(2,2,3,4-Tetramethyl-3-cyclopentenyl)methyl isobutyrate ((R)-(6)) is obtained in step E-1, and (S)-(2,2,3,4-tetramethyl-3-cyclopentenyl)methyl isobutyrate ((S)-(6)) is obtained in step E-2.

The step for obtaining (R)-(2,2,3,4-tetramethyl-3-cyclopentenyl)methyl isobutyrate ((R)-(6)) and a step for obtaining (S)-(2,2,3,4-tetramethyl-3-cyclopentenyl)methyl isobutyrate ((S)-(6)) are carried out under the same reaction conditions. Therefore, only step E-1 for synthesizing (R)-(2,2,3,4-tetramethyl-3-cyclopentenyl)methyl isobutyrate ((R)-(6)) will be described below. The description is applicable also to step E-2 for synthesizing (S)-(2,2,3,4-tetramethyl-3-cyclopentenyl)methyl isobutyrate ((S)-(6)).

(R)-(2,2,3,4-tetramethyl-3-cyclopentenyl)methyl isobutyrate ((R)-(6)) may be synthesized by subjecting (1R,4R)-(3,4,5,5-tetramethyl-2-cyclopentenyl)methyl isobutyrate ((R,R)-(5)) to a double bond migration reaction, as shown in the following chemical reaction formula:

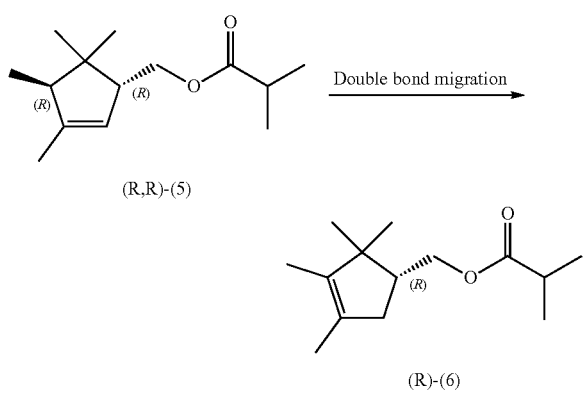

(R,R)-(5)

Double bond migration (R)-(6)

The bold wedged bond and the hashed wedged bonds in the formulae (R,R)-(5) and (R)-(6) represent the absolute configuration.

The double bond migration reaction occurs in the presence of a reagent in a solvent, if needed, with cooling or heating.

Examples of the reagent for the double bond migration reaction include alkaline metal-ethylenediamine in ethylenediamine, such as lithium-ethylenediamine in ethylenediamine; Lewis acids such as boron trifluoride-ethyl ether complex; inorganic acids such as hydrochloric acid, hydrobromic acid, nitric acid, and sulfuric acid; and p-toluenesulfonic acid, trifluoroacetic acid, acetic acid, formic acid, and oxalic acid. p-Toluenesulfonic acid is preferred in view of the reactivity and ease of handling.

An amount of the reagent for the double bond migration reaction is preferably from 0.0001 to 100 mol, more preferably 0.001 to 10 mol, even more preferably 0.01 to 1 mol, per mol of (1R,4R)-(3,4,5,5-tetramethyl-2-cyclopentenyl)methyl isobutyrate ((R,R)-(5)) in view of the reactivity.

Examples of the solvent used in the double bond migration reaction include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Hydrocarbon solvents such as toluene, xylene, and hexane are preferred in view of the reaction rate.

The solvent may be used either alone or in combination thereof, if necessary. The solvent may be commercially available one.

An amount of the solvent used varies, depending on a reaction scale, and is preferably from 200 to 20,000 g, per mol of (1R,4R)-(3,4,5,5-tetramethyl-2-cyclopentenyl) methyl isobutyrate ((R,R)-(5)) in view of the reaction rate.

A reaction temperature in the double bond migration reaction is preferably from −78° C. to a boiling point of the solvent, more preferably 0 to 150° C., in view of the reaction rate and suppression of by-product formation.

A reaction time of the double bond migration reaction varies, depending on a species of a solvent used and/or a reaction scale, and is preferably from 0.1 to 120 hours.

[6] Step F-1 and Step F-2

(1R,4R)-(3,4,5,5-Tetramethyl-2-cyclopentenyl)methanol ((R,R)-(7)) is obtained in step F-1, and (1S,4S)-(3,4,5,5-tetramethyl-2-cyclopentenyl)methanol ((S,S)-(7)) is obtained in step F-2.

The step for obtaining (1R,4R)-(3,4,5,5-tetramethyl-2-cyclopentenyl)methanol ((R,R)-(7)) and the step for obtaining (1S,4S)-(3,4,5,5-tetramethyl-2-cyclopentenyl)methanol ((S,S)-(7)) are carried out in the same reaction conditions. Therefore, only step F-1 for synthesizing (1R,4R)-(3,4,5,5-tetramethyl-2-cyclopentenyl)methanol ((R,R)-(7)) will be described below. The description is applicable also to step F-2 for synthesizing (1S,4S)-(3,4,5,5-tetramethyl-2-cyclopentenyl)methanol ((S,S)-(7)).

(1R,4R)-(3,4,5,5-Tetramethyl-2-cyclopentenyl)methanol ((R,R)-(7)) may be synthesized by subjecting the aforesaid (1R,4R)-(3,4,5,5-tetramethyl-2-cyclopentenyl)methyl isobutyrate ((R,R)-(5)) to (i) a solvolysis reaction or (ii) a reduction reaction, as shown in the following chemical reaction formula:

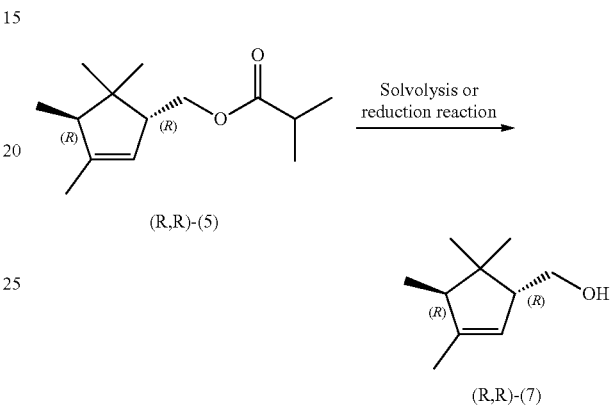

The bold wedged bonds and the hashed wedged bonds in the general formulae (R,R)-(5) and (R,R)-(7) represent the absolute configuration.

(i) Solvolysis Reaction

The conversion of (1R,4R)-(3,4,5,5-tetramethyl-2-cyclopentenyl)methyl isobutyrate ((R,R)-(5)) into (1R,4R)-(3,4,5,5-tetramethyl-2-cyclopentenyl)methanol ((R,R)-(7)) may be done by any known solvolysis reaction of an ester. Examples of the solvolysis reaction include a hydrolysis reaction in a solvent in a basic or neutral condition.

The base, an amount of the base, the salt, an amount of the salt, the solvent, an amount of the solvent, and the reaction temperature and reaction time in the solvolysis reaction are as mentioned for the conversion of the (1S,2R)-(2-hydroxy-3,5,5-trimethyl-3-cyclopentenyl)methyl carboxylate compound ((S,R)-(2)) into (1S,2R)-(2-hydroxy-3,5,5-trimethyl-3-cyclopentenyl)methanol ((S,R)-(1)) in step B-2.

(ii) Reduction Reaction

The conversion of (1R,4R)-(3,4,5,5-tetramethyl-2-cyclopentenyl)methyl isobutyrate ((R,R)-(5)) into (1R,4R)-(3,4,5,5-tetramethyl-2-cyclopentenyl)methanol ((R,R)-(7)) may be done by any known reduction reaction of an ester.

The reducing agent, an amount of the reducing agent, the solvent, an amount of the solvent, and the reaction temperature and reaction time in the reduction reaction are as mentioned for the conversion of the (1S,2R)-(2-hydroxy-3,5,5-trimethyl-3-cyclopentenyl)methyl carboxylate compound ((S,R)-(2)) into (1S,2R)-(2-hydroxy-3,5,5-trimethyl-3-cyclopentenyl)methanol ((S,R)-(1)) in step B-2.

The absolute configurations of (1R,4R)-(3,4,5,5-tetramethyl-2-cyclopentenyl)methanol ((R,R)-(7)) and (1S,4S)-(3,4,5,5-tetramethyl-2-cyclopentenyl)methanol ((S,S)-(7)) synthesized in the processes were confirmed by comparing the GC retention times of these compounds with those of (1R,4R)-(3,4,5,5-tetramethyl-2-cyclopentenyl)methanol and (1S,4S)-(3,4,5,5-tetramethyl-2-cyclopentenyl)methanol ((S,S)-(7)) described in Non-Patent Literature 1 listed above, respectively. Specifically, the absolute configurations were confirmed by comparing the retention times of (R,R)-(7) and (S,S)-(7) using a chiral column Cycodex-B (30 m×0.25 mm×0.25 μm) described in Non-Patent Literature 1.

GC conditions and retention times described in Non-Patent Literature 1 are as shown in the following Table 1.

| Compound | Chiral GC retention time/min |
|---|---|
| 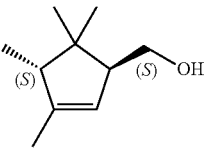 (S,S)-(7) | 23.40 |
| 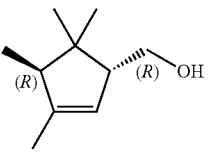 (R,R)-(7) | 23.99 |

Chiral GC column: Cycodex-B (30 m×0.25 mm×0.25 μm)
Temperature program: kept at 50° C. for 1 minute, elevated at a rate of 3° C./minute up to 200° C., and then kept for 4 minutes The GC conditions and retention times for (R,R)-(7) synthesized according to the method described in Example 6 and (S,S)-(7) synthesized according to the method described in Example 11 are as shown in the following Table 2. The absolute configurations were confirmed based on the order of the retention times of the enantiomers.

| Compound | Chiral GC retention time/min |
|---|---|
| 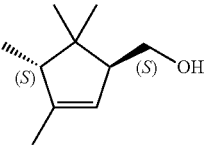 (S,S)-(7) | 28.74 |
| 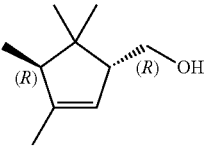 (R,R)-(7) | 29.33 |

Chiral GC column: Cycodex-B (30 m×0.25 mm×0.25 μm)
Temperature program: kept at 50° C. for 1 minute, elevated at a rate of 3° C./minute up to 200° C., and then kept for 4 minutes Next, the absolute configuration of the secondary alcohol obtained by subjecting (1RS,2SR)-(2-hydroxy-3,5,5-trimethyl-3-cyclopentenyl)methyl pivalate ((1RS,2SR)-(2A)) to a kinetic resolution reaction with a lipase in the presence of vinyl acetate was confirmed by the Mosher method with the supposition that the absolute configuration be (1S,2R). Specifically, (1S,2R)-(2-hydroxy-3,5,5-trimethyl-3-cyclopentenyl)methyl pivalate ((S,R)-(2A)) was converted into an (S)-MTPA ester and an (R)-MTPA ester as shown in the chemical formulae in Table 3 below. Differences, δ(S-R) or (Δδ), in $^1$H-NMR chemical shift between the diastereomers were determined. When the MTPA ester group is positioned at the upper side, and the carbinyl proton is positioned at the downside, the proton group of Δδ>0 appears approximately on the right and the proton group of Δδ<0 appears on the left. This confirms that the supposition that the absolute configuration of the secondary alcohol obtained in the kinetic resolution reaction with a lipase be (1S,2R) is right.

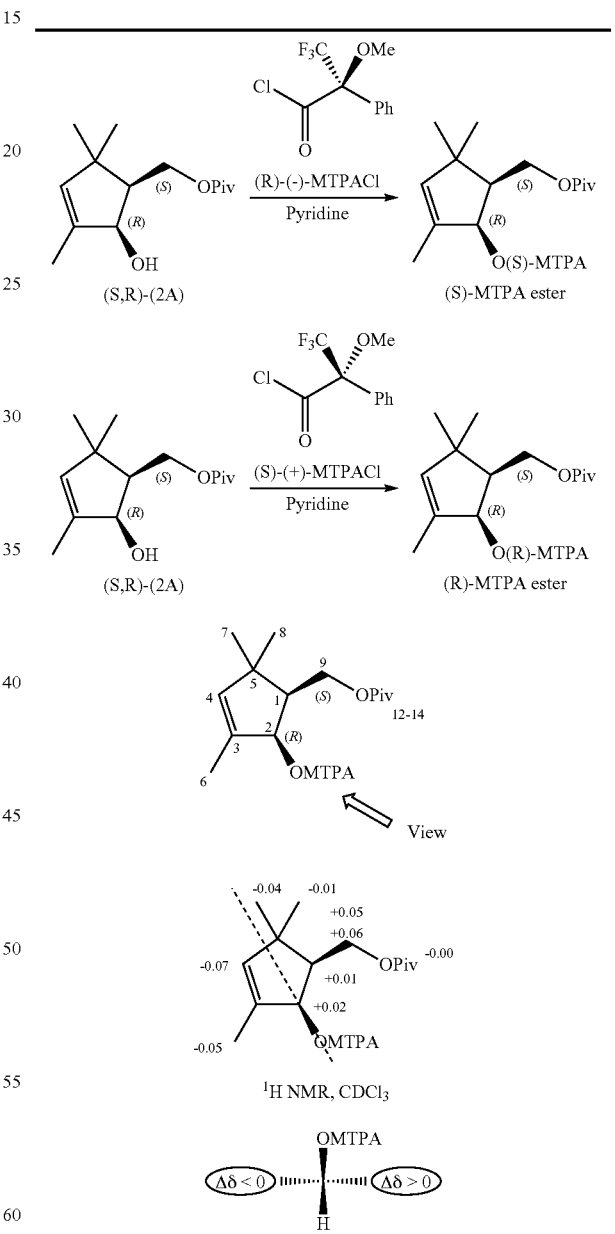

| | $^1$H NMR | | |
|---|---|---|---|
| Position | δ (S) | δ (R) | δ (S-R) |
| 1 | 2.301 | 2.288 | +0.013 |
| 2 | 5.907 | 5.884 | +0.023 |

-continued

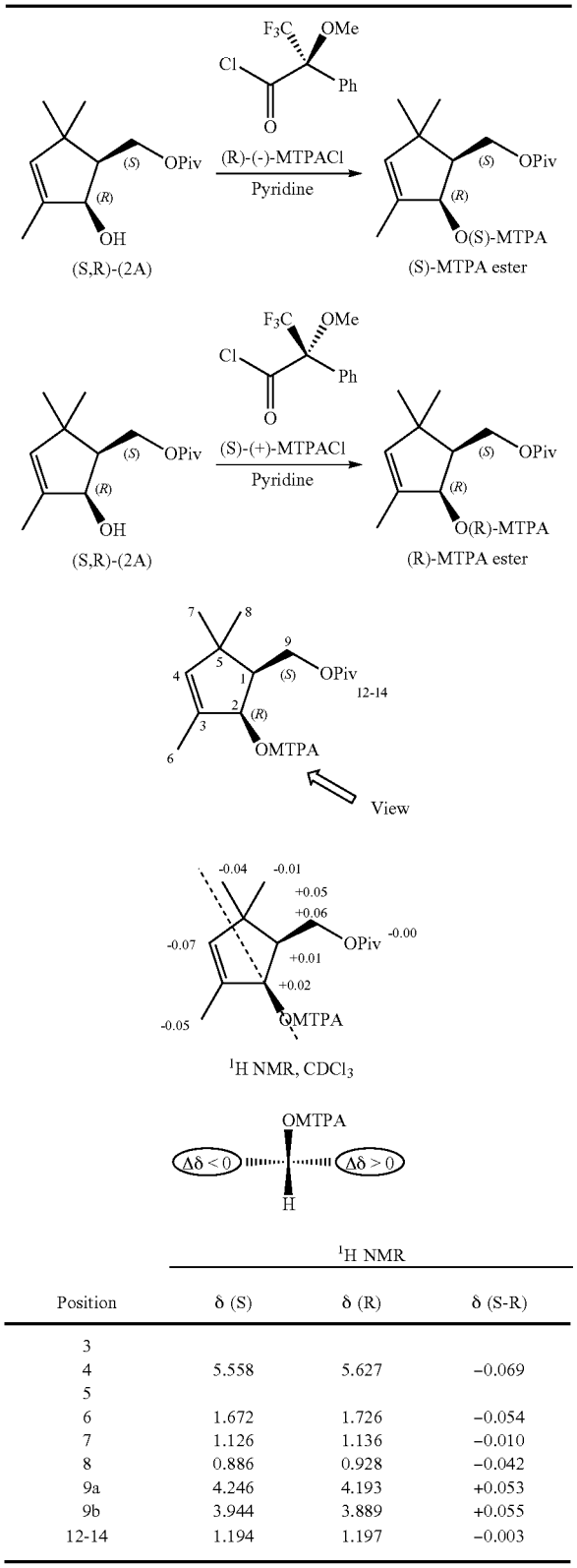

| Position | δ (S) | δ (R) | δ (S-R) |
|---|---|---|---|
| 3 | | | |
| 4 | 5.558 | 5.627 | −0.069 |
| 5 | | | |
| 6 | 1.672 | 1.726 | −0.054 |
| 7 | 1.126 | 1.136 | −0.010 |
| 8 | 0.886 | 0.928 | −0.042 |
| 9a | 4.246 | 4.193 | +0.053 |
| 9b | 3.944 | 3.889 | +0.055 |
| 12-14 | 1.194 | 1.197 | −0.003 |

In the chemical reaction formulae, Piv represents a pivaloyl group, Ph represents a phenyl group, Me represents a methyl group, and MTPA represents an α-methoxy-α-(trifluoromethyl)phenylacetyl group.

EXAMPLES

The present invention will be described with reference to the following Examples. It should be noted that the present invention is not limited to or by the Examples.

The term "yield" as used herein is calculated from the area percentages determined by gas chromatography (hereinafter referred to also as "GC"), unless otherwise specified.

The yield was calculated by the following equation in consideration of purities (% GC) of a starting material and a product.

Yield (%)=[(mass of a product obtained in a reaction×%$GC$)/molecular mass of a product]÷
[(mass of a starting material×%$GC$)/molecular mass of a starting material]}×100

In the Examples, monitoring of the reactions and calculation of the yields were carried out in the following GC conditions.
GC conditions: GC: Capillary gas chromatograph GC-2014 (Shimadzu Corporation); column: DB-5, 30 m×0.25 mm×0.25 μm; carrier gas: He, detector: FID In the Examples, enantiomeric excess was calculated from results obtained in the following GC conditions.
GC conditions: GC: Hewlett-Packard 7890B, column: Cyclodex-B, 30 m×0.25 mm×0.25 μm; carrier gas: He, detector: FID; or GC conditions: GC: Hewlett-Packard 7890B, column: CycloSil-B, 30 m×0.25 mm×0.25 μm; carrier gas: He, detector: FID Example 1: Preparation of (1RS,2SR)-(2-hydroxy-3,5,5-trimethyl-3-cyclopentenyl)methyl pivalate ((RS, SR)-(2A))

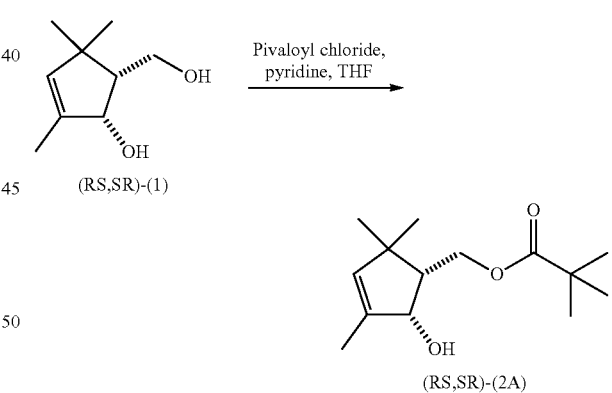

(1RS,2SR)-(2-Hydroxy-3,5,5-trimethyl-3-cyclopentenyl) methanol ((RS,SR)-(1)) (17.0 g, 0.109 mol, racemate), tetrahydrofuran (THF) (54.1 g), and pyridine (31.0 g, 0.392 mol) were placed in a reactor and cooled to 4 to 10° C. Pivaloyl chloride (15.8 g, 0.131 mol) was then added dropwise to the reaction mixture at 15° C. or below. After the completion of the dropwise addition, the reaction mixture was stirred at room temperature for 4 hours and cooled to 4 to 10° C. Brine (172 g: prepared from sodium chloride (16 g) and water (156 g)) was then added to the reaction mixture to quench the reaction. Subsequently, ethyl acetate (67.8 g) was added to the reaction mixture, and the resulting reaction mixture was phase-separated. The organic phase was washed with hydrochloric acid (245 g: prepared from 20 wt % hydrochloric acid (10.2 g), sodium chloride (5.7 g) and water (229 g)), further with brine (235 g: prepared from sodium chloride (5.7 g), and water (229 g)), with an aqueous solution of sodium carbonate (239 g: prepared from sodium carbonate (10.3 g) and water (229 g)), and finally with brine (252 g: prepared from sodium chloride (22.9 g) and water (229 g)). The resulting organic phase was concentrated under reduced pressure, and the concentrate was purified by silica gel column chromatography (eluent: a gradient of n-hexane:ethyl acetate=30:1 to 7:1) to give the target compound, (1RS,2SR)-(2-hydroxy-3,5,5-trimethyl-3-cyclopentenyl)methyl pivalate ((RS,SR)-(2A)) (25.5 g, 0.106 mol, racemate) in a yield of 97.6%.

The following are spectrum data of (1RS,2SR)-(2-hydroxy-3,5,5-trimethyl-3-cyclopentenyl)methyl pivalate ((RS, SR)-(2A)) thus prepared.

Nuclear magnetic resonance spectrum: $^1$H-NMR (500 MHz, CDCl$_3$): δ=1.00 (s, 3H), 1.09 (s, 3H), 1.21 (s, 9H), 1.77 (d, J=1.5 Hz, 3H), 1.97 (ddd, J=9.2, 5.7, 5.7 Hz, 1H), 2.30 (brs, 1H), 4.11 (dd, J=11.1, 5.7 Hz, 1H), 4.30 (d, J=5.7 Hz, 1H), 4.51 (dd, J=11.1, 9.2 Hz, 1H), 5.40 (q, J=1.5 Hz, 1H); $^{13}$C-NMR (75.6 MHz, CDCl$_3$): δ=14.24, 25.22, 27.20 (3C), 28.15, 38.80, 45.17, 52.44, 61.65, 79.18, 138.09, 140.54, 179.38

GC-MS (EI, 70 eV): m/z 240 (M$^+$), 156, 138, 123, 109, 95, 83, 69, 57, 41, 29

Infrared absorption spectrum (NaCl): vmax 3490, 3024, 2960, 2870, 1729, 1711, 1481, 1398, 1288, 1168, 1092, 997, 965, 869, 774

Example 2: Preparation of (1S,2R)-(2-hydroxy-3,5,5-trimethyl-3-cyclopentenyl)methyl pivalate ((S,R)-(2A)) and (1R,2S)-(2-acetoxy-3,5,5-trimethyl-3-cyclopentenyl)methyl pivalate ((R,S)-(3A))

Chemical Corporation) (20.0 g), vinyl acetate (7.07 g, 0.0822 mol), and tert-butyl methyl ether (550 mL) were placed in a reactor and stirred at 48 to 52° C. for 20 hours. Subsequently, the reaction mixture was cooled to room temperature, and the precipitate was filtered off through Celite. The filtrate was concentrated under reduced pressure, and the concentrate was purified by silica gel column chromatography (eluent: a gradient of n-hexane: ethyl acetate=30:1 to 7:1) to give (1S,2R)-(2-hydroxy-3,5,5-trimethyl-3-cyclopentenyl)methyl pivalate ((S,R)-(2A)) (10.6 g, 0.0443 mol, 84.3% ee) in 53.9% yield and (1R,2S)-(2-acetoxy-3,5,5-trimethyl-3-cyclopentenyl)methyl pivalate ((R,S)-(3A)) (10.4 g, 0.0369 mol, 100% ee) in a yield of 44.9%.

(1S,2R)-(2-Hydroxy-3,5,5-trimethyl-3-cyclopentenyl) methyl pivalate ((S,R)-(2A)) thus prepared (10.6 g, 0.0443 mol, 84.3% ee), Lipase AK Amano (FUJIFILM Wako Pure Chemical Corporation) (10.8 g), vinyl acetate (3.81 g, 0.0422 mol), and tert-butyl methyl ether (300 mL) were placed in a reactor and stirred at 48 to 52° C. for 25 hours. Subsequently, the reaction mixture was cooled to room temperature, and the precipitate was filtered off through Celite. The filtrate was concentrated under reduced pressure, and the concentrate was purified by silica gel column chromatography (eluent: a gradient of n-hexane: ethyl acetate=30:1 to 7:1) to give the target compound, (1S,2R)-(2-hydroxy-3,5,5-trimethyl-3-cyclopentenyl)methyl pivalate ((S,R)-(2A)) (9.61 g, 0.0400 mol, 100% ee) in a yield of 90.5%, and (1R,2S)-(2-acetoxy-3,5,5-trimethyl-3-cyclopentenyl)methyl pivalate ((R,S)-(3A)) (0.90 g, 0.0033 mol, 100% ee) in a yield of 7.5%.

Spectrum data of (1S,2R)-(2-hydroxy-3,5,5-trimethyl-3-cyclopentenyl)methyl pivalate ((S,R)-(2A)) thus prepared were in agreement with those of (1RS,2SR)-(2-hydroxy-3,

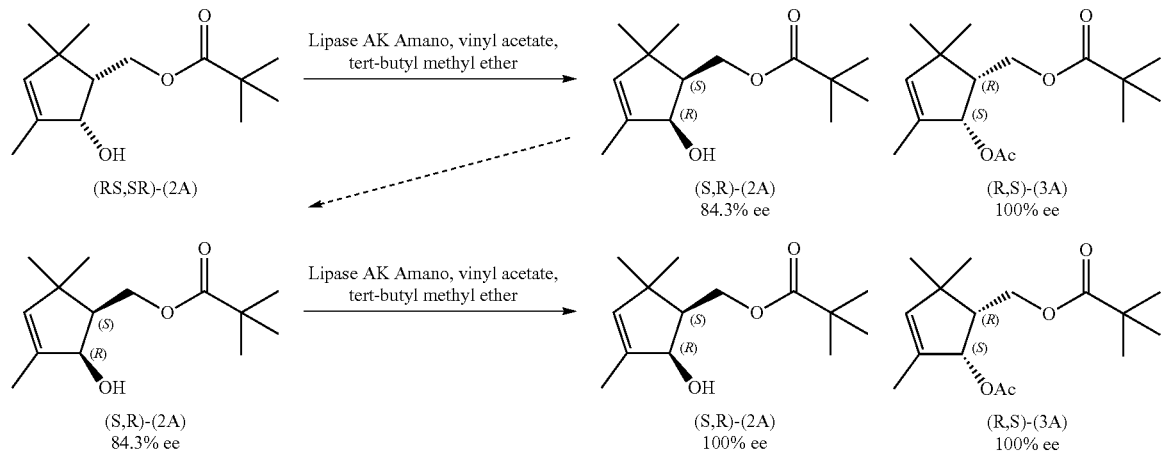

wherein Ac represents an acetyl group.

(1RS,2SR)-(2-Hydroxy-3,5,5-trimethyl-3-cyclopentenyl) methyl pivalate ((RS,SR)-(2A)) prepared according to the procedures described in Example 1 (19.8 g, 0.0822 mol, racemate), Lipase AK Amano (FUJIFILM Wako Pure 5,5-trimethyl-3-cyclopentenyl)methyl pivalate ((RS,SR)-(2A)) obtained in Example 1.

The following are spectrum data of (1R,2S)-(2-acetoxy-3,5,5-trimethyl-3-cyclopentenyl)methyl pivalate ((R,S)-(3A)) thus prepared.

Nuclear magnetic resonance spectrum: $^1$H-NMR (500 MHz, CDCl$_3$): δ=1.00 (s, 3H), 1.13 (s, 3H), 1.17 (s, 9H), 1.67 (d, J=1.5 Hz, 3H), 2.02 (s, 3H), 2.27 (ddd, J=8.8, 6.5, 6.5, 1H), 4.11 (dd, J=11.1, 8.8 Hz, 1H), 4.18 (dd, J=11.1, 6.5 Hz, 1H), 5.49 (q, J=1.5 Hz, 1H), 5.70 (d, J=6.5 Hz, 1H); $^{13}$C-NMR (75.6 MHz, CDCl$_3$): δ=14.29, 21.01, 24.39, 27.12 (3C), 28.00, 38.67, 45.23, 50.05, 60.85, 80.42, 135.16, 143.21, 170.57, 178.55

LC-MS (ESI, positive): m/z 300 (M$^+$+18)

Infrared absorption spectrum (NaCl): νmax 2960, 2871, 1734, 1481, 1370, 1283, 1233, 1156, 1088, 1017, 979, 919, 771, 607, 527

Example 3: Preparation of (1R,2S)-(2-hydroxy-3,5,5-trimethyl-3-cyclopentenyl)methanol ((R,S)-(1))

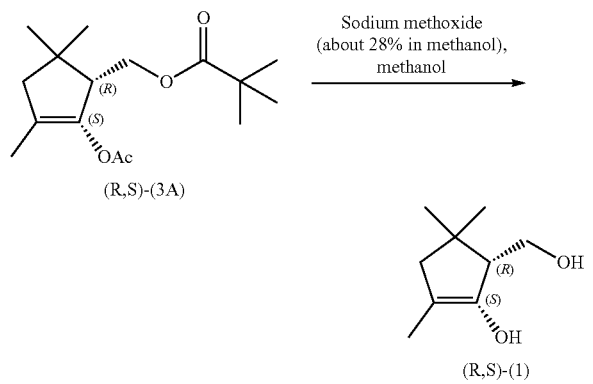

wherein Ac represents an acetyl group.

(1R,2S)-(2-Acetoxy-3,5,5-trimethyl-3-cyclopentenyl) methyl pivalate ((R,S)-(3A)) obtained according to Example 2 (9.71 g, 0.0344 mol, 100% ee) and methanol (230 mL) were placed in a reactor and stirred at room temperature. Sodium methoxide (about 28% in methanol) (6.64 g, 0.0344 mol) was added dropwise at room temperature, and the reaction mixture was then stirred at 60 to 65° C. for 3.5 hours. Subsequently, the reaction mixture was cooled to 4 to 10° C., and brine (253 g: prepared from sodium chloride (23 g) and water (230 g)) was added. Ethyl acetate (500 mL) was further added and the mixture was phase-separated to give an organic phase and an aqueous phase. The aqueous phase was subjected to extraction with ethyl acetate (200 mL). The organic phase obtained in this extraction was combined with the organic phase obtained in the phase separation, dried over sodium sulfate, and filtered to remove the sodium sulfate. The resulting organic phase was concentrated under reduced pressure, and the concentrate was purified by silica gel column chromatography (eluent: a gradient of n-hexane: ethyl acetate=3:1 to 2:3) to quantitatively yield the target compound, (1R,2S)-(2-hydroxy-3,5,5-trimethyl-3-cyclopentenyl)methanol ((R,S)-(1)) (5.37 g, 0.0344 mol, 99.9% ee).

The following are the spectrum data and specific rotation of (1R,2S)-(2-hydroxy-3,5,5-trimethyl-3-cyclopentenyl) methanol ((R,S)-(1)) thus prepared.

Nuclear magnetic resonance spectrum: $^1$H-NMR (500 MHz, CDCl$_3$): δ=0.97 (s, 3H), 1.06 (s, 3H), 1.77-1.78 (m, 3H), 2.05 (ddd, J=10.0, 6.5, 5.4 Hz, 1H), 3.79 (dd, J=10.7, 5.4 Hz, 1H), 3.95 (dd, J=10.7, 10.0 Hz, 1H), 4.58 (d, J=6.5 Hz, 1H), 5.39 (q, J=1.5 Hz, 1H). A peak of the hydroxy group was unobserved possibly due to replacement of deuterium present in a trace amount in the solvent with protium; $^{13}$C-NMR (75.6 MHz, CDCl$_3$): δ=13.96, 25.46, 28.92, 44.67, 54.14, 59.86, 80.37, 137.91, 140.81

GC-MS (EI, 70 eV): m/z 156 (M$^+$), 141, 125, 109, 95, 77, 67, 55, 43, 29

Infrared absorption spectrum (NaCl): νmax 3312, 3021, 2971, 2946, 2862, 1443, 1404, 1215, 1112, 1091, 1030, 971, 952, 902, 873, 772, 718, 644, 594

Specific rotation [α]$_D^{25}$ -117 (c 1.01, EtOH)

Example 4: Preparation of (1R,2S)-(3,5,5-trimethyl-2-isobutyryloxy-3-cyclopentenyl)methyl isobutyrate ((R,S)-(4))

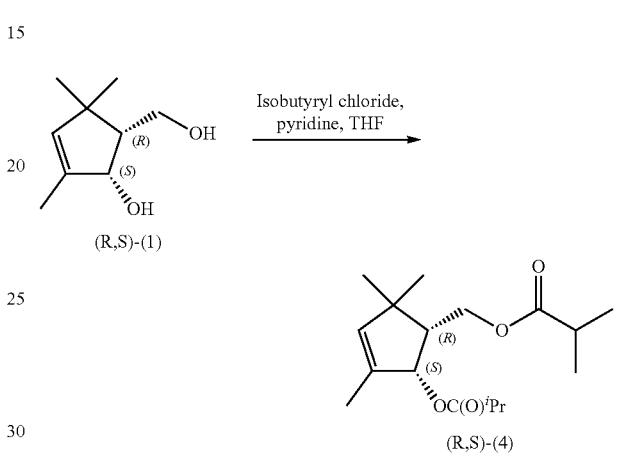

wherein $^i$Pr represents an isopropyl group.

(1R,2S)-(2-Hydroxy-3,5,5-trimethyl-3-cyclopentenyl) methanol ((R,S)-(1)) prepared according to the procedures described in Example 3 (5.01 g, 0.0321 mol, 99.9% ee), THF (79.8 g), and pyridine (11.5 g, 0.145 mol) were placed in a reactor and cooled to 4 to 10° C. Isobutyryl chloride (10.3 g, 0.0966 mol) was then added dropwise to the reaction mixture at 10° C. or below. After the completion of the dropwise addition, the reaction mixture was stirred at 4 to 10° C. for 6 hours. Brine (211 g: prepared from sodium chloride (19.2 g) and water (192 g)) was then added to the reaction mixture to quench the reaction. Subsequently, hexane (99.8 g) was added to the reaction mixture, and the resulting reaction mixture was phase-separated. The organic phase was washed with hydrochloric acid (361 g: prepared from 20 wt % hydrochloric acid (15.0 g), sodium chloride (8.4 g) and water (338 g)). Further, the organic phase was washed with brine (346 g: prepared from sodium chloride (8.4 g) and water (338 g)), an aqueous solution of sodium carbonate (353 g: prepared from sodium carbonate (15.1 g) and water (353 g)), and then brine (372 g: prepared from sodium chloride (33.8 g) and water (338 g)). The resulting organic phase was concentrated under reduced pressure, and the concentrate was purified by silica gel column chromatography (eluent: a gradient of n-hexane: ethyl acetate=100:1 to 20:1) to give the target compound, (1R, 2S)-(3,5,5-trimethyl-2-isobutyryloxy-3-cyclopentenyl) methyl isobutyrate ((R,S)-(4)) (9.04 g, 0.0305 mol) in a yield of 95.1%.

The following are the spectrum data and specific rotation of (1R,2S)-(3,5,5-trimethyl-2-isobutyryloxy-3-cyclopentenyl)methyl isobutyrate ((R,S)-(4)) thus prepared.

Nuclear magnetic resonance spectrum: $^1$H-NMR (500 MHz, CDCl$_3$): δ1.00 (s, 3H), 1.12 (s, 3H), 1.12-1.15 (m, 12H), 1.65 (d, J=1.5 Hz, 3H), 2.28 (ddd, J=9.2, 6.5, 6.5 Hz, 1H), 2.48-2.54 (m, 2H), 4.11 (dd, J=11.1, 6.5 Hz, 1H), 4.17 (dd, J=11.1, 9.2 Hz, 1H), 5.49 (q, J=1.5 Hz, 1H), 5.70 (d, J=6.5 Hz, 1H); $^{13}$C-NMR (75.6 MHz, CDCl$_3$): δ14.30, 18.89, 18.94, 19.04 (2C), 24.48, 27.84, 33.98, 34.28, 45.21, 50.19, 60.69, 79.97, 135.32, 143.10, 176.51, 177.07

LC-MS (ESI, positive): m/z 314 (M$^+$+18)

Infrared absorption spectrum (NaCl): vmax 2972, 2874, 1734, 1471, 1386, 1256, 1192, 1157, 1115, 1087, 983, 961, 900, 850, 756

Specific rotation $[\alpha]_D^{24}$-160 (c 1.00, CHCl$_3$)

Example 5: Preparation of (1R,4R)-(3,4,5,5-tetramethyl-2-cyclopentenyl)methyl isobutyrate ((R,R)-(5))

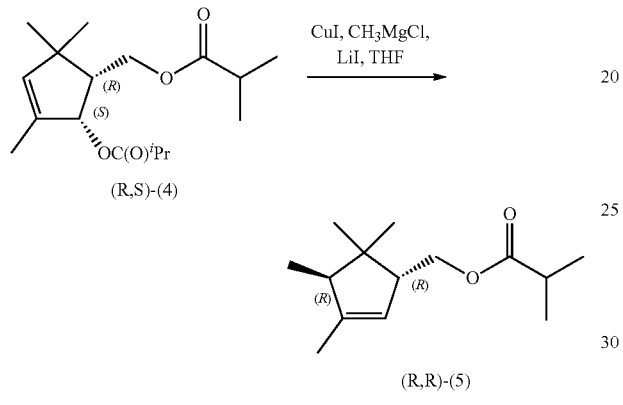

wherein $^i$Pr represents an isopropyl group.

Copper (I) iodide (8.13 g, 0.0427 mol) and THF (76.0 g) were placed in a reactor and cooled to 0 to 4° C. Lithium iodide (11.4 g, 0.0852 mol) was then added at 10° C. or below. Subsequently, a 0.00258 mol/g solution of methylmagnesium chloride in THF (33.1 g, 0.0854 mol) was added dropwise at 10° C. or below. After the completion of the dropwise addition, the resulting reaction mixture was stirred at 0 to 4° C. for 30 minutes to prepare a solution of the methylating agent in THF.

Next, (1R,2S)-(3,5,5-trimethyl-2-isobutyryloxy-3-cyclopentenyl)methyl isobutyrate ((R,S)-(4)) prepared according to the procedures described in Example 4 (8.45 g, 0.0285 mol) and THF (25.0 g) were placed in another reactor and stirred at 37 to 42° C. for 30 minutes. The aforesaid solution of the methylating agent in THF was then added dropwise at 35 to 45° C. After the completion of the dropwise addition, the reaction mixture was stirred at 37 to 42° C. for 5 hours. After the completion of the stirring, the reaction mixture was cooled to 4 to 10° C., and an aqueous solution of ammonium chloride (33.7 g: prepared from ammonium chloride (3.1 g) and water (30.6 g)) was added to quench the reaction. Further, 20 wt % hydrochloric acid (6.1 g) and hexane (114 g) were added to the resulting reaction mixture, and the reaction mixture was phase-separated. The organic phase was washed with aqueous ammonia (169 g: prepared from ammonium chloride (5.5 g) and 25 wt % aqueous sodium hydroxide (18.3 g) and water (145 g)) four times. The washed organic phase was further washed with brine (151 g: prepared from sodium chloride (5.6 g) and water (145 g)). The resulting organic phase was concentrated under reduced pressure, and the concentrate was purified by silica gel column chromatography (eluent: a gradient of n-hexane: ethyl acetate=100:1 to 80:1) to give the target compound, (1R,4R)-(3,4,5,5-tetramethyl-2-cyclopentenyl)methyl isobutyrate ((R,R)-(5)) (5.90 g, 0.0263 mol) in a yield of 92.3%.

The following are the spectrum data and specific rotation of (1R,4R)-(3,4,5,5-tetramethyl-2-cyclopentenyl)methyl isobutyrate ((R,R)-(5)) thus prepared.

Nuclear magnetic resonance spectrum: $^1$H-NMR (500 MHz, CDCl$_3$): δ0.88 (d, J=7.3 Hz, 3H), 0.95 (s, 3H), 0.96 (s, 3H), 1.16 (d, J=6.9 Hz, 6H), 1.65 (q, J=1.9 Hz, 3H), 2.10-2.15 (m, 1H), 2.45-2.49 (m, 1H), 2.49-2.56 (m, 1H), 3.93 (dd, J=11.1, 6.9 Hz, 1H), 4.10 (dd, J=11.1, 6.5 Hz, 1H), 5.14-5.15 (m, 1H); $^{13}$C-NMR (75.6 MHz, CDCl$_3$): δ12.36, 15.17, 18.97, 19.00, 23.95, 24.59, 34.13, 43.01, 52.52, 52.61, 64.59, 123.03, 145.27, 177.21

GC-MS (EI, 70 eV): m/z 224 (M$^+$), 136, 121, 105, 93, 81, 67, 55, 43, 27

Infrared absorption spectrum (NaCl): vmax 3040, 2966, 2873, 1737, 1470, 1387, 1258, 1191, 1157, 1074, 982, 919, 826, 755

Specific rotation $[\alpha]_D^{25}$-158 (c 1.02, CHCl$_3$)

Example 6: Preparation of (1R,4R)-(3,4,5,5-tetramethyl-2-cyclopentenyl)methanol ((R,R)-(7))

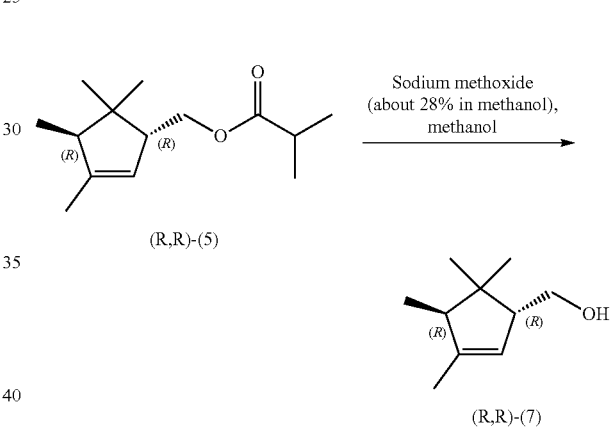

(1R,4R)-(3,4,5,5-Tetramethyl-2-cyclopentenyl)methyl isobutyrate ((R,R)-(5)) obtained according to Example 5 (5.90 g, 0.0263 mol) and methanol (200 mL) were placed in a reactor and stirred at room temperature. Sodium methoxide (about 28% in methanol) (5.21 g, 0.0270 mol) was added dropwise at room temperature, and then the reaction mixture was stirred at 58 to 62° C. for 4 hours. Subsequently, the reaction mixture was cooled to 4 to 10° C., and brine (220 g: prepared from sodium chloride (20 g) and water (200 g)) was added. Ethyl acetate (400 mL) was further added and the mixture was phase-separated to give an organic phase and an aqueous phase. The aqueous phase was subjected to extraction with ethyl acetate (150 mL), and the organic phase obtained from this extraction was combined with the organic phase obtained in the phase separation and washed with saturated brine (600 mL). The organic phase was dried over sodium sulfate and filtered to remove sodium sulfate. The resulting organic phase was concentrated under reduced pressure, and the concentrate was purified by silica gel column chromatography (eluent: a gradient of n-hexane: ethyl acetate=20:1 to 9:1) to give the target compound, (1R,4R)-(3,4,5,5-tetramethyl-2-cyclopentenyl)methanol ((R,R)-(7)) (3.42 g, 0.0222 mol, 99.6% ee) in a yield of 84.4%.

The following are the spectrum data and specific rotation of (1R,4R)-(3,4,5,5-tetramethyl-2-cyclopentenyl)methanol ((R,R)-(7)) thus prepared.

Nuclear magnetic resonance spectrum: $^1$H-NMR (500 MHz, CDCl$_3$): δ=0.87 (d, J=7.3 Hz, 3H), 0.91 (s, 3H), 0.99 (s, 3H), 1.54 (brs, 1H), 1.67 (q, J=1.9 Hz, 3H), 2.15-2.20 (m, 1H), 2.27-2.31 (m, 1H), 3.55, (dd, J=10.7, 6.5 Hz, 1H), 3.62 (dd, J=10.7, 5.4 Hz, 1H), 5.23-5.24 (m, 1H); $^{13}$C-NMR (75.6 MHz, CDCl$_3$): δ=11.95, 15.18, 23.54, 24.93, 42.94, 52.15, 56.36, 63.09, 123.19, 145.70

GC-MS (EI, 70 eV): m/z 154, 139, 123, 105, 91, 81, 67, 55, 41, 31

Infrared absorption spectrum (NaCl): νmax 3330, 2962, 2870, 1655, 1445, 1364, 1199, 1071, 1030, 1016, 957, 828

Specific rotation $[\alpha]_D^{27}$-168 (c 1.02, CHCl$_3$)

Example 7: Preparation of (R)-(2,2,3,4-tetramethyl-3-cyclopentenyl)methyl isobutyrate ((R)-(6))

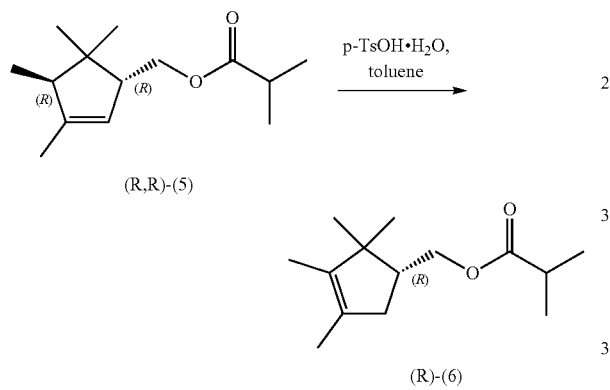

(1R,4R)-(3,4,5,5-Tetramethyl-2-cyclopentenyl)methyl isobutyrate ((R,R)-(5)) obtained in Example 5 (0.59 g, 2.6 mmol), p-toluenesulfonic acid monohydrate (p-TsOH·H$_2$O) (0.04 g, 0.2 mmol), and toluene (20 mL) were placed in a reactor and stirred at 100 to 110° C. for 5 hours. The reaction mixture was then cooled to 4 to 10° C., and an aqueous solution of sodium bicarbonate (10.1 g: prepared from sodium bicarbonate (0.10 g) and water (10 g)) was added to quench the reaction. The resulting reaction mixture was phase-separated, and the organic phase was washed with saturated brine (30 mL). The resulting organic phase was concentrated under reduced pressure, and the concentrate was purified by silica gel column chromatography (eluent: a gradient of n-hexane: ethyl acetate=100:1 to 80:1) to give the target compound, (R)-(2,2,3,4-tetramethyl-3-cyclopentenyl)methyl isobutyrate ((R)-(6)) (0.44 g, 2.0 mmol) in a yield of 75%.

The following are the spectrum data and specific rotation of (R)-(2,2,3,4-tetramethyl-3-cyclopentenyl)methyl isobutyrate ((R)-(6)) thus prepared.

Nuclear magnetic resonance spectrum: $^1$H-NMR (500 MHz, CDCl$_3$): δ=0.82 (s, 3H), 1.05 (s, 3H), 1.168 (d, J=6.9 Hz, 3H), 1.169 (d, J=6.9 Hz, 3H), 1.47-1.48 (m, 3H), 1.57-1.59 (m, 3H), 1.95-2.01 (m, 1H), 2.09-2.15 (m, 1H), 2.21-2.26 (m, 1H), 2.54 (septet, J=6.9 Hz, 1H), 4.09 (dd, J=11.1, 7.7 Hz, 1H), 4.15 (dd, J=11.1, 6.9 Hz, 1H); $^{13}$C-NMR (75.6 MHz, CDCl$_3$): δ=9.20, 14.09, 18.99, 19.02, 19.92, 27.01, 34.12, 39.06, 46.74, 47.67, 65.62, 127.85, 138.52, 177.27

GC-MS (EI, 70 eV): m/z 224 (M$^+$), 136, 121, 105, 93, 79, 67, 55, 43, 27

Infrared absorption spectrum (NaCl): νmax 2967, 2929, 1737, 1470, 1386, 1360, 1261, 1193, 1157, 1073, 979, 919

Specific rotation $[\alpha]_D^{25}$-8.2 (c 1.01, CHCl$_3$)

Example 8: Preparation of (1S,2R)-(2-hydroxy-3,5,5-trimethyl-3-cyclopentenyl)methanol ((S,R)-(1))

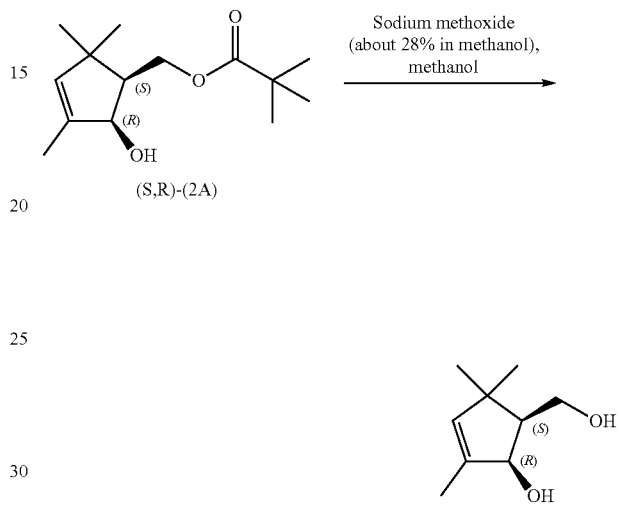

(1S,2R)-(2-Hydroxy-3,5,5-trimethyl-3-cyclopentenyl) methyl pivalate ((S,R)-(2A)) prepared according to the procedures described in Example 2 (9.83 g, 0.0409 mol, 100% ee), and methanol (300 mL) were placed in a reactor and stirred at room temperature. Sodium methoxide (about 28% in methanol) (7.89 g, 0.0409 mol) was added dropwise at room temperature. The reaction mixture was then stirred at 60 to 65° C. for 5.5 hours. Subsequently, the reaction mixture was cooled to 4 to 10° C., and brine (330 g: prepared from sodium chloride (30 g) and water (300 g)) was added. Ethyl acetate (600 mL) was further added and the mixture was phase-separated to give an organic phase and an aqueous phase. The aqueous phase was subjected to extraction with ethyl acetate (200 mL), and the organic phase obtained from this extraction was combined with the organic phase obtained in the phase separation, dried over sodium sulfate, and filtered to remove sodium sulfate. The resulting organic phase was concentrated under reduced pressure, and the concentrate was purified by silica gel column chromatography (eluent: a gradient of n-hexane: ethyl acetate=3:1 to 2:3) to give the target compound, (1S,2R)-(2-hydroxy-3,5,5-trimethyl-3-cyclopentenyl)methanol ((S,R)-(1)) (5.69 g, 0.0364 mol, 99.7% ee) in a yield of 89.0%.

The spectrum data of (1S,2R)-(2-hydroxy-3,5,5-trimethyl-3-cyclopentenyl)methanol ((S,R)-(1)) thus prepared were in agreement with those of (1R,2S)-(2-hydroxy-3,5,5-trimethyl-3-cyclopentenyl)methanol ((R,S)-(1)) obtained in Example 3.

Specific rotation $[\alpha]_D^{26}$+118 (c 1.01, EtOH)

The value of the specific rotation was almost in agreement with the absolute value of the specific rotation obtained in Example 3.

Example 9: Preparation of (1S,2R)-(3,5,5-trimethyl-2-isobutyryloxy-3-cyclopentenyl)methyl isobutyrate ((S,R)-(4))

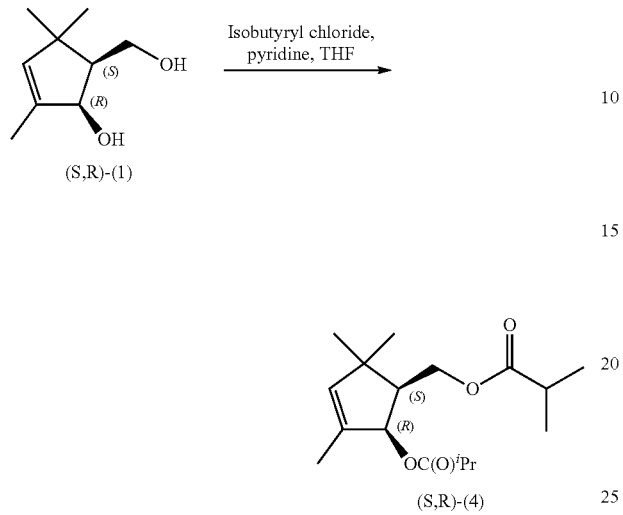

wherein $^i$Pr represents an isopropyl group.

(1S,2R)-(2-Hydroxy-3,5,5-trimethyl-3-cyclopentenyl)methanol ((S,R)-(1)) prepared according to the procedures described in Example 8 (5.44 g, 0.0348 mol, 99.7% ee), THF (86.5 g), and pyridine (12.3 g, 0.156 mol) were placed in a reactor and cooled to 4 to 10° C. Isobutyryl chloride (11.2 g, 0.105 mol) was then added dropwise to the reaction mixture at 10° C. or below. After the completion of the dropwise addition, the reaction mixture was stirred at 4 to 10° C. for 6 hours. Brine (229 g: prepared from sodium chloride (20.8 g) and water (208 g)) was then added to the reaction mixture to quench the reaction. Subsequently, hexane (108 g) was added to the reaction mixture, and the resulting reaction mixture was phase-separated. The organic phase was washed with hydrochloric acid (391 g: prepared from 20 wt % hydrochloric acid (16.3 g), sodium chloride (9.1 g) and water (366 g)). Further, the organic phase was washed with brine (375 g: prepared from sodium chloride (9.1 g) and water (366 g)), an aqueous solution of sodium carbonate (382 g: prepared from sodium carbonate (16.4 g) and water (366 g)), and then brine (403 g: prepared from sodium chloride (36.6 g) and water (366 g)). The resulting organic phase was concentrated under reduced pressure, and the concentrate was purified by silica gel column chromatography (eluent: a gradient of n-hexane: ethyl acetate=100:1 to 20:1) to give the target compound, (1S,2R)-(3,5,5-trimethyl-2-isobutyryloxy-3-cyclopentenyl)methyl isobutyrate ((S,R)-(4)) (10.1 g, 0.0342 mol) in a yield of 98.2%.

The spectrum data of (1S,2R)-(3,5,5-trimethyl-2-isobutyryloxy-3-cyclopentenyl)methyl isobutyrate ((S,R)-(4)) were in agreement with those of (1R,2S)-(3,5,5-trimethyl-2-isobutyryloxy-3-cyclopentenyl)methyl isobutyrate ((R,S)-(4)) obtained in Example 4.

Specific rotation $[\alpha]_D^{25}$+158 (c 1.01, CHCl$_3$)

The value of the specific rotation was almost in agreement with the absolute value of the specific rotation obtained in Example 4.

Example 10: Preparation of (1S,4S)-(3,4,5,5-tetramethyl-2-cyclopentenyl)methyl isobutyrate ((S,S)-(5))

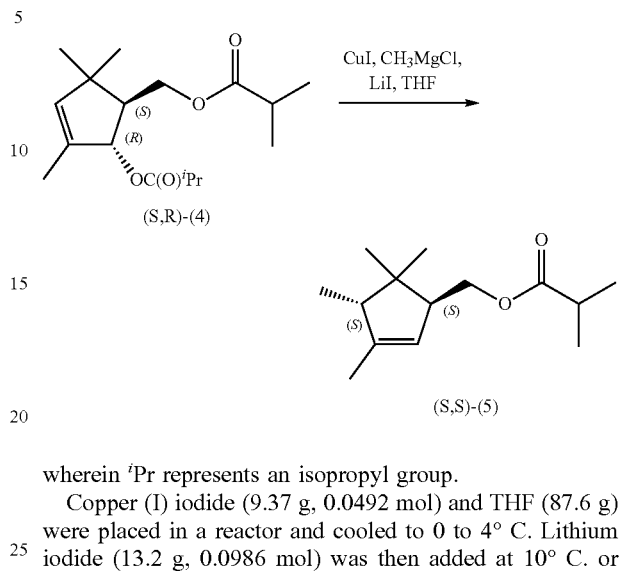

wherein $^i$Pr represents an isopropyl group.

Copper (I) iodide (9.37 g, 0.0492 mol) and THF (87.6 g) were placed in a reactor and cooled to 0 to 4° C. Lithium iodide (13.2 g, 0.0986 mol) was then added at 10° C. or below. Subsequently, a 0.00258 mol/g solution of methylmagnesium chloride in THF (38.1 g, 0.0982 mol) was added dropwise at 10° C. or below. After the completion of the dropwise addition, the resulting reaction mixture was stirred at 0 to 4° C. for 30 minutes to prepare a solution of a methylating agent in THF.

Next, (1S,2R)-(3,5,5-trimethyl-2-isobutyryloxy-3-cyclopentenyl)methyl isobutyrate ((S,R)-(4)) prepared according to the procedures described in Example 9 (9.72 g, 0.0328 mol) and THF (18.4 g) were placed in another reactor and stirred at 37 to 42° C. for 30 minutes. The aforesaid solution of the methylating agent in THF was then added dropwise at 35 to 45° C. After the completion of the dropwise addition, the reaction mixture was stirred at 37 to 42° C. for 4 hours. After the completion of the stirring, the reaction mixture was cooled to 4 to 10° C., and an aqueous solution of ammonium chloride (38.7 g: prepared from ammonium chloride (3.5 g) and water (35.2 g)) was added to quench the reaction. Further, 20 wt % hydrochloric acid (7.0 g) and hexane (131 g) were added to the resulting reaction mixture, and the reaction mixture was phase-separated. The organic phase was washed with aqueous ammonia (194 g: prepared from ammonium chloride (6.3 g), 25 wt % aqueous sodium hydroxide (21.1 g) and water (167 g)) four times. The washed organic phase was further washed with brine (173 g: prepared from sodium chloride (6.4 g) and water (167 g)). The resulting organic phase was concentrated under reduced pressure, and the concentrate was purified by silica gel column chromatography (eluent: a gradient of n-hexane: ethyl acetate=100:1 to 80:1) to give the target compound, (1S,4S)-(3,4,5,5-tetramethyl-2-cyclopentenyl)methyl isobutyrate ((S,S)-(5)) (6.39 g, 0.0285 mol) in a yield of 86.9%.

The spectrum data of (1S,4S)-(3,4,5,5-tetramethyl-2-cyclopentenyl)methyl isobutyrate ((S,S)-(5)) thus prepared were in agreement with those of (1R,4R)-(3,4,5,5-tetramethyl-2-cyclopentenyl)methyl isobutyrate ((R,R)-(5)) obtained in Example 5.

Specific rotation $[\alpha]_D^{24}$+156 (c 1.01, CHCl$_3$)

The value of the specific rotation was almost in agreement with the absolute value of the specific rotation obtained in Example 5.

Example 11: Preparation of (1S,4S)-(3,4,5,5-tetramethyl-2-cyclopentenyl)methanol ((S,S)-(7))

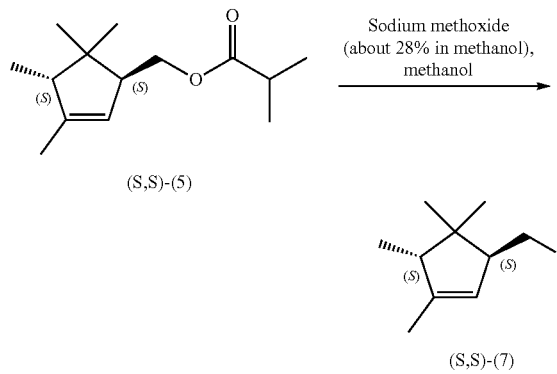

(1S,4S)-3,4,5,5-Tetramethyl-2-cyclopentenyl)methyl isobutyrate ((S,S)-(5)) obtained according to Example 10 (6.39 g, 0.0285 mol) and methanol (225 mL) were placed in a reactor and stirred at room temperature. Sodium methoxide (about 28% in methanol) (6.14 g, 0.0318 mol) was added dropwise at room temperature, and the reaction mixture was then stirred at 58 to 62° C. for 9.5 hours. Subsequently, the reaction mixture was cooled to 4 to 10° C., and brine (248 g: prepared from sodium chloride (22.5 g) and water (225 g)) was added. Ethyl acetate (450 mL) was further added and the mixture was phase-separated to give an organic phase and an aqueous phase. The aqueous phase was subjected to extraction with ethyl acetate (150 mL), and the organic phase obtained from this extraction was combined with the organic phase obtained in the phase separation and washed with saturated brine (600 mL). The organic phase was dried over sodium sulfate and filtered to remove sodium sulfate. The resulting organic phase was concentrated under reduced pressure, and the concentrate was purified by silica gel column chromatography (eluent: a gradient of n-hexane: ethyl acetate=20:1 to 9:1) to give the target compound, (1S,4S)-(3,4,5,5-tetramethyl-2-cyclopentenyl)methanol ((S,S)-(7)) (3.69 g, 0.0239 mol, 99.3% ee) in a yield of 84.0%.

The spectrum data of (1S,4S)-(3,4,5,5-tetramethyl-2-cyclopentenyl)methanol ((S,S)-(7)) thus prepared were in agreement with those of (1R,4R)-(3,4,5,5-tetramethyl-2-cyclopentenyl)methanol ((R,R)-(7)) obtained in Example 6.

Specific rotation $[\alpha]_D^{24}$+163 (c 1.00, CHCl$_3$)

The value of the specific rotation was almost in agreement with the absolute value of the specific rotation obtained in Example 6.

Example 12: Preparation of (S)-(2,2,3,4-tetramethyl-3-cyclopentenyl)methyl isobutyrate ((S)-(6))

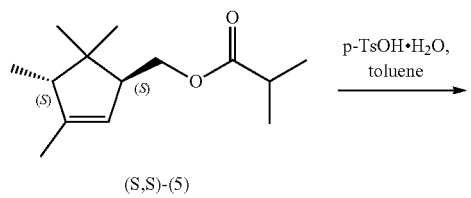

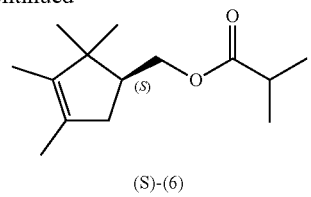

(1S,4S)-(3,4,5,5-Tetramethyl-2-cyclopentenyl)methyl isobutyrate ((S,S)-(5)) obtained in Example 10 (0.29 g, 1.3 mmol), p-toluenesulfonic acid monohydrate (p-TsOH·H$_2$O) (0.03 g, 0.2 mmol), and toluene (25 mL) were placed in a reactor and stirred at 100 to 110° C. for 10 hours. Subsequently, the reaction mixture was cooled to 4 to 10° C., and an aqueous solution of sodium bicarbonate (10.1 g: prepared from sodium bicarbonate (0.1 g) and water (10 g)) was added to quench the reaction. The resulting reaction mixture was phase-separated, and the organic phase was washed with saturated brine (30 mL). The resulting organic phase was concentrated under reduced pressure, and the concentrate was purified by silica gel column chromatography (eluent: a gradient of n-hexane: ethyl acetate=100:1 to 80:1) to give the target compound, (S)-(2,2,3,4-tetramethyl-3-cyclopentenyl)methyl isobutyrate ((S)-(6)) (0.24 g, 1.1 mmol) in a yield of 84%.

The spectrum data of the (S)-(2,2,3,4-tetramethyl-3-cyclopentenyl)methyl isobutyrate ((S)-(6)) thus prepared were in agreement with those of (R)-(2,2,3,4-tetramethyl-3-cyclopentenyl)methyl isobutyrate ((R)-(6)) obtained in Example 7.

Specific rotation $[\alpha]_D^{24}$+9.0 (c 1.01, CHCl$_3$)

The value of the specific rotation was almost in agreement with the absolute value of the specific rotation obtained in Example 7.

The invention claimed is:

1. A process for preparing a (1S,2R)-(2-hydroxy-3,5,5-trimethyl-3-cyclopentenyl)methyl carboxylate compound of the following general formula (S,R)-(2):

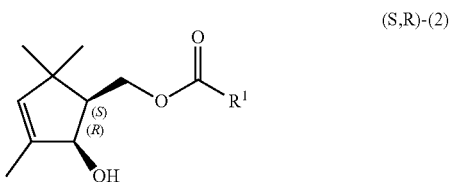

wherein R$^1$ represents a monovalent hydrocarbon group having 1 to 6 carbon atoms, and a bold wedged bond represents the absolute configuration, and a (1R,2S)-(2-acetoxy-3,5,5-trimethyl-3-cyclopentenyl)methyl carboxylate compound of the following general formula (R,S)-(3):

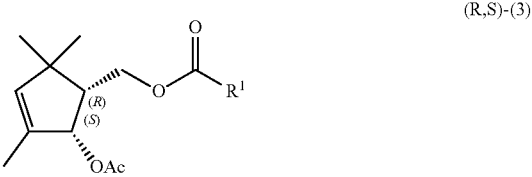

wherein $R^1$ is as defined above, a hashed wedged bond represents the absolute configuration, and Ac represents an acetyl group, the process comprising:
subjecting a (1RS,2SR)-(2-hydroxy-3,5,5-trimethyl-3-cyclopentenyl)methyl carboxylate compound of the following general formula (RS,SR)-(2):

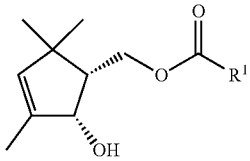

(RS,SR)-(2)

wherein $R^1$ is as defined above, and a hashed unwedged bond represents a relative configuration,
to a kinetic resolution reaction with a lipase in the presence of vinyl acetate to obtain the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)).

2. A process for preparing (1R,4R)-(3,4,5,5-tetramethyl-2-cyclopentenyl)methyl isobutyrate of the following formula (R,R)-(5):

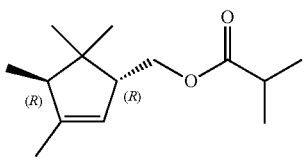

(R,R)-(5)

wherein a hashed wedged bond and a bold wedged bond represent the absolute configuration, the process comprising:
the process according to claim 1 for preparing the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)), and
subjecting the (1R,2S)-(2-acetoxy-3,5,5-trimethyl-3-cyclopentenyl)methyl carboxylate compound ((R,S)-(3)) thus obtained to a solvolysis reaction or a reduction reaction to form (1R,2S)-(2-hydroxy-3,5,5-trimethyl-3-cyclopentenyl)methanol of the following formula (R,S)-(1):

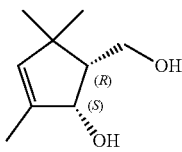

(R,S)-(1)

wherein a hashed wedged bond represents the absolute configuration,
subjecting (1R,2S)-(2-hydroxy-3,5,5-trimethyl-3-cyclopentenyl)methanol ((R,S)-(1)) thus obtained to an isobutyrylation reaction to form (1R,2S)-(3,5,5-trimethyl-2-isobutyryloxy-3-cyclopentenyl)methyl isobutyrate of the following formula (R,S)-(4):

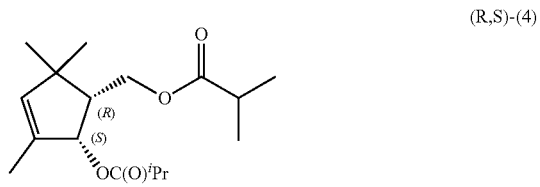

(R,S)-(4)

wherein a hashed wedged bond represents the absolute configuration, and $^i$Pr represents an isopropyl group, and
subjecting (1R,2S)-(3,5,5-trimethyl-2-isobutyryloxy-3-cyclopentenyl)methyl isobutyrate ((R,S)-(4)) thus obtained to a nucleophilic substitution reaction with a methylating agent (8) of the following general formula (8):

$$CH_3\text{-}M \quad (8)$$

wherein M represents Li, $MgZ^1$, $ZnZ^1$, Cu, $CuZ^1$, or $CuLiZ^1$, wherein $Z^1$ represents a halogen atom or a methyl group,
to form (1R,4R)-(3,4,5,5-tetramethyl-2-cyclopentenyl)methyl isobutyrate ((R,R)-(5)).

3. A process for preparing (1S,4S)-(3,4,5,5-tetramethyl-2-cyclopentenyl)methyl isobutyrate of the following formula (S,S)-(5):

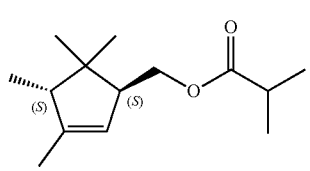

(S,S)-(5)

wherein a hashed wedged bond and a bold wedged bond represent the absolute configuration, the process comprising:
the process according to claim 1 for preparing the (1S,2R)-(2-hydroxy-3,5,5-trimethyl-3-cyclopentenyl)methyl carboxylate compound ((S,R)-(2)) and the (1R,2S)-(2-acetoxy-3,5,5-trimethyl-3-cyclopentenyl)methyl carboxylate compound ((R,S)-(3)), and
subjecting the (1S,2R)-(2-hydroxy-3,5,5-trimethyl-3-cyclopentenyl)methyl carboxylate compound ((S,R)-(2)) thus obtained to a solvolysis reaction or a reduction reaction to form (1S,2R)-(2-hydroxy-3,5,5-trimethyl-3-cyclopentenyl)methanol of the following formula (S,R)-(1):

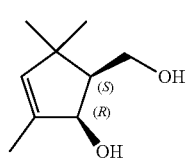

(S,R)-(1)

wherein a bold wedged bond represents the absolute configuration, subjecting (1S,2R)-(2-hydroxy-3,5,5-trimethyl-3-cyclopentenyl)methanol ((S,R)-(1)) thus obtained to an isobutyrylation reaction to form (1S,2R)-(3,5,5-trimethyl-2-isobutyryloxy-3-cyclopentenyl)methyl isobutyrate of the following formula (S,R)-(4):

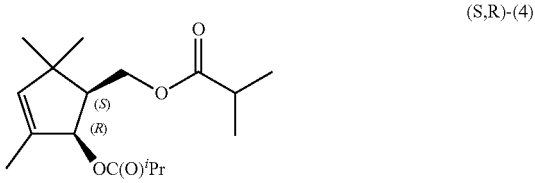

(S,R)-(4)

wherein a bold wedged bond represents the absolute configuration, and $^i$Pr represents an isopropyl group, and subjecting (1S,2R)-(3,5,5-trimethyl-2-isobutyryloxy-3-cyclopentenyl)methyl isobutyrate ((S,R)-(4)) thus obtained to a nucleophilic substitution reaction with a methylating agent (8) of the following general formula (8):

$$CH_3\text{-}M \quad (8)$$

wherein M represents Li, MgZ$^1$, ZnZ$^1$, Cu, CuZ$^1$, or CuLiZ$^1$, wherein Z$^1$ represents a halogen atom or a methyl group to form (1S,4S)-(3,4,5,5-tetramethyl-2-cyclopentenyl)methyl isobutyrate ((S,S)-(5)).

4. A process for preparing (R)-(2,2,3,4-tetramethyl-3-cyclopentenyl)methyl isobutyrate of the following formula (R)-(6):

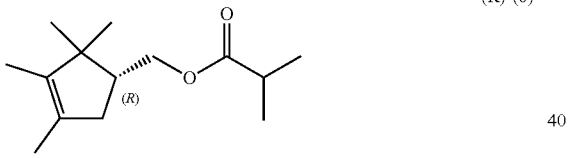

(R)-(6)

wherein a hashed wedged bond represents the absolute configuration, the process comprising:

the process according to claim 2 for preparing (1R,4R)-(3,4,5,5-tetramethyl-2-cyclopentenyl)methyl isobutyrate ((R,R)-(5)), and subjecting (1R,4R)-(3,4,5,5-tetramethyl-2-cyclopentenyl)methyl isobutyrate ((R,R)-(5)) thus obtained to a double bond migration reaction to form (R)-(2,2,3,4-tetramethyl-3-cyclopentenyl)methyl isobutyrate ((R)-(6)).

5. A process for preparing (S)-(2,2,3,4-tetramethyl-3-cyclopentenyl)methyl isobutyrate of the following formula (S)-(6):

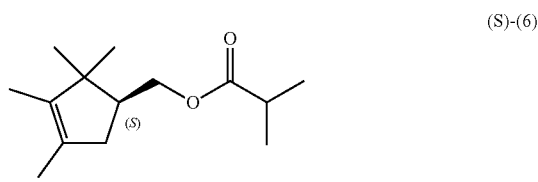

(S)-(6)

wherein a bold wedged bond represents the absolute configuration, the process comprising:

the process according to claim 3 for preparing (1S,4S)-(3,4,5,5-tetramethyl-2-cyclopentenyl)methyl isobutyrate ((S,S)-(5)), and subjecting (1S,4S)-(3,4,5,5-tetramethyl-2-cyclopentenyl)methyl isobutyrate ((S,S)-(5)) thus obtained to a double bond migration reaction to form (S)-(2,2,3,4-tetramethyl-3-cyclopentenyl)methyl isobutyrate ((S)-(6)).

* * * * *

UNITED STATES PATENT AND TRADEMARK OFFICE
CERTIFICATE OF CORRECTION

PATENT NO. : 11,746,078 B2
APPLICATION NO. : 17/580874
DATED : September 5, 2023
INVENTOR(S) : Watanabe et al.

Page 1 of 2

It is certified that error appears in the above-identified patent and that said Letters Patent is hereby corrected as shown below:

In the Specification

Column 16, Line 52: Please correct "(1R,25)" to read --(1R,2S)--

Column 16, Line 55: Please correct "(1R,25)" to read --(1R,2S)--

Column 16, Line 58: Please correct "(1R,25)" to read --(1R,2S)--

Column 18, Lines 7-8: Please correct "available 1 one." to read --available one.--

Column 24, Line 35: Please correct "available 1 one." to read --available one.--

Column 26, Line 4: Please correct "(1R,25)" to read --(1R,2S)--

Column 31, Lines 1-49: Please delete the formulas

Column 35, Lines 19-33: Please delete the formula and replace with the following:

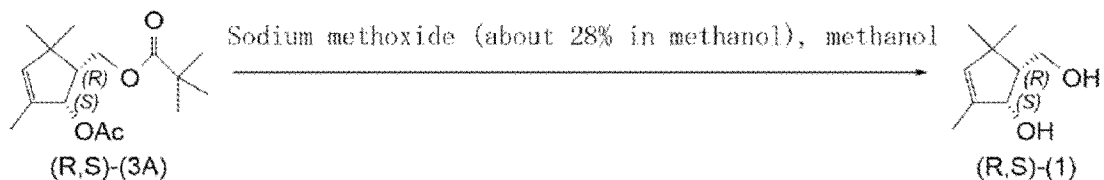

Signed and Sealed this
Second Day of April, 2024

Katherine Kelly Vidal
*Director of the United States Patent and Trademark Office*

Column 42, Lines 5-20: Please delete the formula and replace with the following:
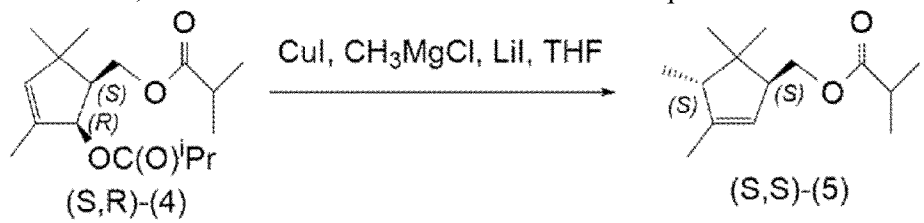
Column 43, Line 43: Please correct "(1S,45)" to read --(1S,4S)--
Column 44, Line 11: Please correct "(1S,45)" to read --(1S,4S)--